US012735693B2

(12) United States Patent
Shirai et al.

(10) Patent No.: US 12,735,693 B2
(45) Date of Patent: Sep. 15, 2026

(54) METHOD FOR PRODUCING CHAIN UNSATURATED CARBOXYLIC ACID COMPOUND USING PHENYLALANINE AMMONIA LAYSE

(71) Applicants: RIKEN, Wako (JP); ZEON CORPORATION, Tokyo (JP); THE YOKOHAMA RUBBER CO., LTD., Hiratsuka (JP)

(72) Inventors: Tomokazu Shirai, Wako (JP); Yutaro Mori, Wako (JP); Yoshihide Yachi, Tokyo (JP); Misao Hiza, Hiratsuka (JP); Yayoi Akahori, Hiratsuka (JP)

(73) Assignees: RIKEN, Wako (JP); ZEON CORPORATION, Tokyo (JP); THE YOKOHAMA RUBBER CO., LTD., Hiratsuka (JP)

( * ) Notice: Subject to any disclaimer, the term of this patent is extended or adjusted under 35 U.S.C. 154(b) by 424 days.

(21) Appl. No.: 18/269,745

(22) PCT Filed: Dec. 7, 2021

(86) PCT No.: PCT/JP2021/044890

§ 371 (c)(1),
(2) Date: Jun. 26, 2023

(87) PCT Pub. No.: WO2022/145178

PCT Pub. Date: Jul. 7, 2022

(65) Prior Publication Data

US 2025/0320481 A1 Oct. 16, 2025

(30) Foreign Application Priority Data

Dec. 28, 2020 (JP) ................................ 2020-219017

(51) Int. Cl.

| | |
|---|---|
| ***C12N 9/88*** | (2006.01) |
| ***C12N 15/70*** | (2006.01) |
| ***C12P 5/00*** | (2006.01) |
| ***C12P 5/02*** | (2006.01) |
| ***C12P 7/40*** | (2006.01) |
| ***C12R 1/19*** | (2006.01) |

(52) U.S. Cl.

CPC ............... *C12N 9/88* (2013.01); *C12N 15/70* (2013.01); *C12P 5/007* (2013.01); *C12P 5/026* (2013.01); *C12P 7/40* (2013.01); *C12R 2001/19* (2021.05); *C12Y 401/01* (2013.01); *C12Y 403/01024* (2013.01)

(58) Field of Classification Search

None

See application file for complete search history.

(56) References Cited

U.S. PATENT DOCUMENTS

| | | | | |
|---|---|---|---|---|
| 2013/0005012 | A1 | 1/2013 | Yu | |
| 2015/0337336 | A1 | 11/2015 | Bhuiya et al. | |
| 2016/0030194 | A1 | 2/2016 | Ledet et al. | |
| 2020/0017845 | A1* | 1/2020 | Novick .......... | C12Y 403/01024 |
| 2020/0048674 | A1* | 2/2020 | Chang ..................... | C12P 13/04 |

FOREIGN PATENT DOCUMENTS

| | | | |
|---|---|---|---|
| JP | 2014-030376 | A | 2/2014 |
| JP | 2015-228804 | A | 12/2015 |
| WO | 2019/022083 | A1 | 1/2019 |
| WO | 2020/013951 | A1 | 1/2020 |

OTHER PUBLICATIONS

Hanson et al., Phenylalanine Ammonia-lyase: Enzymic Conversion of 3-( 1,4-Cyclohexadienyl)-L-alanine to trans-3-(I,4-Cyclohexadienyl)acrylic Acid, Biochemistry 18, 1979, 1431-38. (Year: 1979).*

Weiser et al., Phenylalanine Ammonia-Lyase-Catalyzed Deamination of an Acyclic Amino Acid, ChemBioChem 16, 2015, 2283-88. (Year: 2015).*

Jul. 4, 2023 International Preliminary Report on Patentability issued in International Patent Application No. PCT/JP2021/044890.

Mar. 8, 2022 International Search Report issued in International Patent Application No. PCT/JP2021/044890.

Karl A. P. Payne et al.; "New cofactor supports alpha, beta-unsaturated acid decarboxylation via 1,3-dipolar cycloaddition"; Nature; Jun. 2015; vol. 522; Issue 7557; pp. 497-501.

J.A. Marchand et al.; "Discovery of a pathway for terminal-alkyne amino acid biosynthesis"; Nature; Mar. 2019; vol. 567; Issue 7748; pp. 420-424.

* cited by examiner

*Primary Examiner* — Todd M Epstein
(74) *Attorney, Agent, or Firm* — Oliff PLC

(57) ABSTRACT

A method for producing a chain-shaped unsaturated carboxylic acid compound or a geometric isomer thereof, having at least two carbon-carbon double bonds, including the steps of: removing, from a chain-shaped unsaturated carboxylic acid compound or a geometric isomer thereof having an amino group and a carbon-carbon double bond at a terminus, that amino group, in the presence of phenylalanine ammonia lyase, and further forming a carbon-carbon double bond.

4 Claims, 2 Drawing Sheets

Specification includes a Sequence Listing.

Butadiene

Fig. 3

| | F94 | L104 | F107 | L108 | L171 | L219 | N223 | K419 | I423 | Q448 | E452 |
|---|---|---|---|---|---|---|---|---|---|---|---|
| G | 0.0 | 0.4 | 0.2 | 0.2 | 0.0 | 0.0 | 0.0 | 0.0 | 0.0 | 0.0 | 0.0 |
| A | 0.0 | 1.3 | 0.4 | 0.6 | 0.0 | 0.0 | 0.0 | 0.0 | 0.1 | 0.0 | 0.0 |
| V | 0.1 | 0.2 | 0.1 | 1.4 | 0.0 | 0.1 | 0.1 | 0.0 | 0.7 | 0.0 | 0.0 |
| I | 0.1 | 0.2 | 0.0 | 0.7 | 0.3 | 1.6 | 1.6 | 0.0 | | 0.0 | 0.0 |
| L | 0.2 | | 0.2 | | | | | 0.0 | 0.7 | 0.0 | 0.0 |
| M | 0.0 | 0.3 | 0.2 | 5.2 | 0.1 | 0.0 | 0.0 | 0.0 | 0.9 | 0.0 | 0.0 |
| F | | 0.2 | | 3.1 | 0.0 | 0.0 | 0.0 | 0.0 | 0.3 | 0.0 | 0.2 |
| Y | 0.4 | 0.0 | 0.2 | 0.0 | 0.0 | 0.0 | 0.0 | 0.0 | 0.0 | 0.0 | 0.0 |
| W | 0.2 | 0.0 | 5.1 | 0.0 | 0.0 | 0.0 | 0.0 | 0.0 | 0.0 | 0.0 | 0 |

METHOD FOR PRODUCING CHAIN UNSATURATED CARBOXYLIC ACID COMPOUND USING PHENYLALANINE AMMONIA LAYSE

SEQUENCE LISTING

The present application contains a Sequence Listing that has been submitted electronically in ASCII format and is hereby incorporated by reference in its entirety. The ASCII copy, created on Jan. 24, 2024, is named Substitute_Sequence_Listing_ST25.txt and is 80,772 bytes in size.

TECHNICAL FIELD

The present invention relates to a method for producing a third chain-shaped unsaturated carboxylic acid compound by introducing a further carbon-carbon double bond into a second chain-shaped unsaturated carboxylic acid compound having a carbon-carbon double bond at the terminus, in the presence of phenylalanine ammonia lyase. In addition, the present invention relates to a method for producing a second chain-shaped unsaturated carboxylic acid compound from a first chain-shaped unsaturated carboxylic acid compound having an amino group at the terminus, in the presence of terminal alkene-producing enzyme BesC, and then, from this compound, producing a third chain-shaped unsaturated carboxylic acid compound in the presence of phenylalanine ammonia lyase. Furthermore, the present invention relates to a method for producing such a third chain-shaped unsaturated carboxylic acid compound and then, in the presence of ferulic acid decarboxylase, producing a chain-shaped unsaturated hydrocarbon compound having carbon-carbon double bonds at both terminuses from the unsaturated carboxylic acid compound.

The present invention also relates to a phenylalanine ammonia lyase variant that can be used in these production methods, a DNA encoding the variant, a vector into which the DNA has been inserted, and a host cell into which the DNA or vector has been introduced. Furthermore, the present invention relates to a method for producing the variant using the aforementioned host cell.

BACKGROUND ART

It can be said that butadiene (1,3-butadiene) is an extremely important organic compound in the chemical industry because it is used as a raw material for various polymer compounds, including various synthetic rubbers (such as butadiene rubber, styrene-butadiene rubber, and acrylonitrile-butadiene rubber), and polymer resins (such as ABS resin and Nylon 66). In addition, these polymer compounds using butadiene as a raw material are widely used not only for industrial products such as automobile tires but also for daily necessities such as clothing. Therefore, the demand for butadiene is increasing year by year. Its annual demand is 13 million tons, and the market size has reached 15 billion dollars.

Conventionally, butadiene has been produced by purifying the C4 fraction produced as a byproduct mainly in the process of producing ethylene and propylene from petroleum. However, due to environmental problems including the depletion of fossil fuels such as petroleum and global warming due to greenhouse gas emissions, there is an increasing need to achieve sustainable butadiene production to meet the above-mentioned increasing demand for butadiene. As a countermeasure against these problems, development has been actively conducted of a method which uses an enzyme to produce butadiene from a biomass resource-derived material that is a renewable resource.

For example, PTL 1 discloses a method for producing butadiene by using xylose as a raw material and a microorganism having an enzyme activity capable of converting xylose into crotyl alcohol or the like. In addition, PTL 2 discloses a method for producing butadiene by using xylose as a raw material and a microorganism having an enzyme activity capable of converting xylose into 2,3-butanediol. Many attempts have been made to produce unsaturated hydrocarbon compounds such as butadiene using an enzyme as described above.

Furthermore, it has been revealed by the present inventors that the production of 4-vinylguaiacol (4VG) by the decarboxylation reaction of ferulic acid involving ferulic acid decarboxylase (FDC) (see NPL 1) can be applied to the production of unsaturated hydrocarbon compounds such as butadiene (PTL 3). That is, it has been found by the present inventors that butadiene and the like can be produced through the decarboxylation reaction as shown in the following formula, using FDC, from muconic acid and the like.

[Chem. 1]

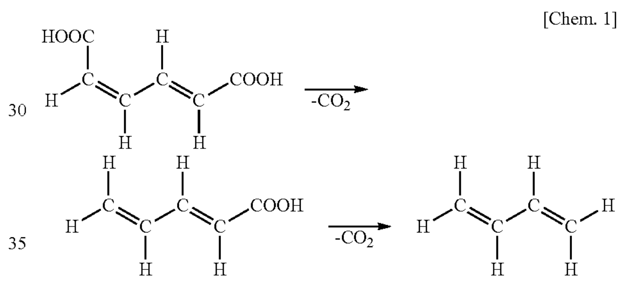

However, due to the high cost of muconic acid, there are concerns that it could hinder practical application. Therefore, it is desirable to develop a method for producing unsaturated compounds, such as butadiene, which have at least two carbon-carbon double bonds, more inexpensively using enzymes.

CITATION LIST

Patent Literature

[PTL 1] Japanese Patent Application Publication No. 2014-30376

[PTL 2] Japanese Patent Application Publication No. 2015-228804

[PTL 3] International Publication No. WO2019-022083

Non Patent Literature

[NPL 1] Karl A. P. Payne et al., Nature. 2015, volume 522, issue 7557, pp. 497 to 501

[NPL 2]J A Marchand et al., Nature, 2019, volume 567, issue 7748, pp. 420 to 424

SUMMARY OF INVENTION

Technical Problem

The present invention has been made in view of the above-described problems of the related art, and an object thereof is to provide a method for producing an unsaturated compound having at least two carbon-carbon double bonds using an enzyme.

Solution to Problem

The present inventors, in an effort to achieve the aforementioned objects, conducted intensive research and subsequently conceived the following reaction scheme to produce butadiene using L-lysine instead of muconic acid as the starting material. Note that L-lysine can be obtained relatively inexpensively, which can help control costs in the production of butadiene.

[Chem. 2]

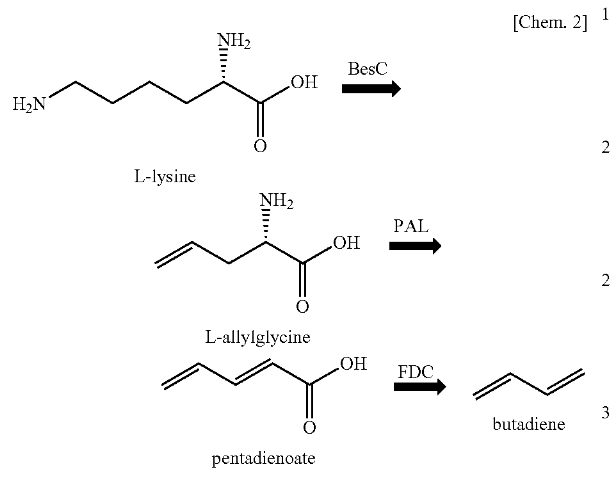

L-lysine

L-allylglycine pentadienoate butadiene

Furthermore, the present inventors conceived that the enzyme BesC disclosed in NPL 2 could be used in the production of L-allylglycine from L-lysine. This enzyme has an activity to catalyze a reaction that forms a carbon-carbon double bond at the terminus by oxidizing the propylamino group at the terminus to cleave the carbon-carbon bond within this group. In addition, they conceived that FDC, which has been revealed by the present inventors as described above, could be used in the production of butadiene from pentadienoate (PTL 3).

However, no reports of enzymes that could contribute to the production of pentadienoate from L-allylglycine were found. Therefore, the present inventors considered whether phenylalanine ammonia lyase (PAL), which is involved in the production of cinnamic acid from phenylalanine, could be utilized for this purpose.

[Chem. 3]

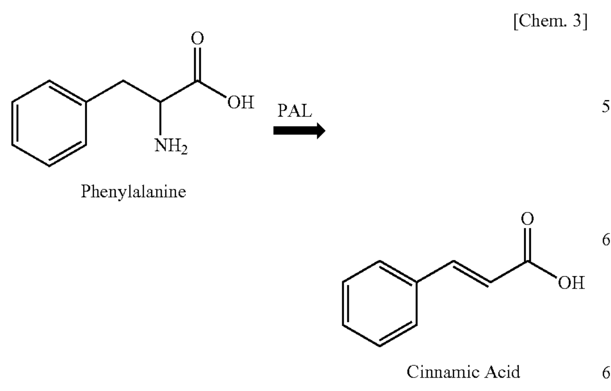

Phenylalanine

Cinnamic Acid

Then, in practice, *E. coli* that highly expressed BesC and PAL derived from *Arabidopsis thaliana* (AtPAL) were cultivated. The resultant cell lysate obtained through processing was mixed with the cell lysate obtained from the cultivation and processing of *E. coli* that highly expressed FDC. Upon the addition of L-lysine, it was clearly revealed that butadiene was produced.

Furthermore, the present inventors verified butadiene production in the same manner for PALs derived from different sources (PAL from *Anabaena variabilis* (AvPAL), and PAL from *Plagiochasma appendiculatum* (PaPAL)). As a result, it was revealed that butadiene could be produced in the same way as with AtPAL using either AvPAL or PaPAL. Moreover, among these, the present inventors found that AvPAL had outstanding catalytic activity related to the production of pentadienoate.

Furthermore, regarding this AvPAL, the present inventors introduced a variety of amino acid substitutions and verified their impact on butadiene production. As a result, they found that the butadiene production quantity improved in comparison to the wild type prior to introduction in any of the following amino acid substitutions (1) to (5), leading to the completion of the present invention:

(1) substitution of leucine at position 108 with methionine, phenylalanine, or valine,
(2) substitution of phenylalanine at position 107 with tryptophan,
(3) substitution of leucine at position 219 with isoleucine,
(4) substitution of asparagine at position 223 with isoleucine,
(5) substitution of leucine at position 104 with alanine.

Specifically, the present invention relates to a method for producing a third chain-shaped unsaturated carboxylic acid compound by introducing a further carbon-carbon double bond into a second chain-shaped unsaturated carboxylic acid compound having a carbon-carbon double bond at the terminus, in the presence of PAL. In addition, the present invention relates to a method for producing a second chain-shaped unsaturated carboxylic acid compound from a first chain-shaped unsaturated carboxylic acid compound having an amino group at the terminus, in the presence of BesC, and then, from this compound, producing a third chain-shaped unsaturated carboxylic acid compound in the presence of phenylalanine ammonia lyase. Furthermore, the present invention relates to a method for producing such a third chain-shaped unsaturated carboxylic acid compound and, in the presence of PDC, producing a chain-shaped unsaturated hydrocarbon compound having carbon-carbon double bonds at both terminuses from the unsaturated carboxylic acid compound.

The present invention also relates to a PAL mutant that can be used in these production methods, a DNA encoding the mutant, a vector into which the DNA has been inserted, and a host cell into which the DNA or vector has been introduced. Furthermore, the present invention relates to a method for producing the mutant using the aforementioned host cell.

More specifically, the present invention provides the following.

[1]A method for producing a chain-shaped unsaturated carboxylic acid compound or a geometric isomer thereof, represented by the following formula (3), including the steps of: removing a first amino group from a chain-shaped unsaturated carboxylic acid compound or a geometric isomer thereof, having a first amino group and a first carbon-carbon double bond at a terminus, represented by the following formula (2), in the presence of phenylalanine ammonia lyase, and forming a second carbon-carbon double bond

[Chem. 4]

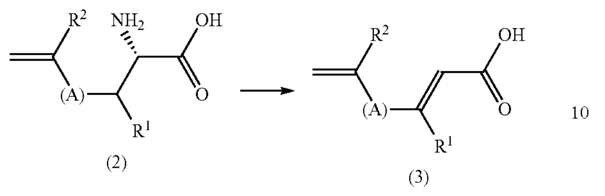

(2)

(3)

[in the formulas, (A) represents a linear hydrocarbon group having 0 to 5 carbon atoms, which may be substituted, and when the number of carbon atoms is 2 to 5, it may form a double bond between adjacent carbon atoms. $R^1$ and $R^2$ each independently represent a hydrogen atom, a linear or branched alkyl group having 1 to 5 carbon atoms, a linear or branched alkoxy group having 1 to 5 carbon atoms, or a hydroxy group.].

[2] The method according to [1], further including the steps of: removing a second amino group and a methylene group from a chain-shaped carboxylic acid compound or a geometric isomer thereof, having a first amino group and a second amino group at a terminus, represented by the following formula (1), in the presence of the terminal alkene generating enzyme BesC, and producing a chain-shaped unsaturated carboxylic acid compound or a geometric isomer thereof, represented by the formula (2), wherein the compound or a geometric isomer thereof is used to produce the chain-shaped unsaturated carboxylic acid compound or a geometric isomer thereof, represented by the formula (3)

[Chem. 5]

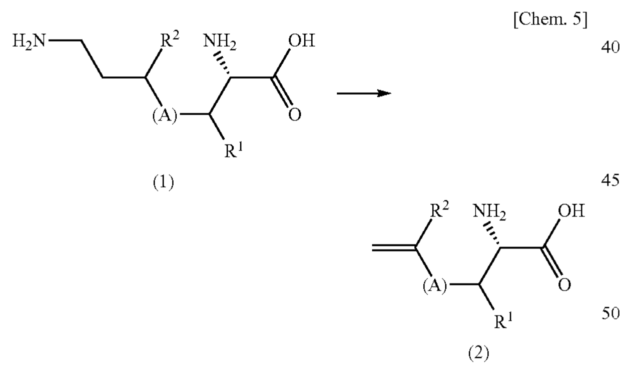

(1)

(2)

[in the formulas, (A) represents a linear hydrocarbon group having 0 to 5 carbon atoms, which may be substituted, and when the number of carbon atoms is 2 to 5, it may form a double bond between adjacent carbon atoms. $R^1$ and $R^2$ each independently represent a hydrogen atom, a linear or branched alkyl group having 1 to 5 carbon atoms, a linear or branched alkoxy group having 1 to 5 carbon atoms, or a hydroxy group.].

[3]A method for producing a chain-shaped unsaturated hydrocarbon compound or a geometric isomer thereof, represented by the following formula (4), further including the steps of: producing the chain-shaped unsaturated carboxylic acid compound or a geometric isomer thereof, represented by the formula (3) by the method according to [1] or [2], and decarboxylating a carboxyl group from the unsaturated carboxylic acid compound or a geometric isomer thereof, in the presence of ferulic acid decarboxylase

[Chem. 6]

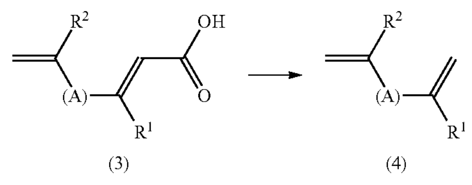

(3)

(4)

[in the formulas, (A) represents a linear hydrocarbon group having 0 to 5 carbon atoms, which may be substituted, and when the number of carbon atoms is 2 to 5, it may form a double bond between adjacent carbon atoms. $R^1$ and $R^2$ each independently represent a hydrogen atom, a linear or branched alkyl group having 1 to 5 carbon atoms, a linear or branched alkoxy group having 1 to 5 carbon atoms, or a hydroxy group.].

[4] The method according to any one of [1] to [3], where the phenylalanine ammonia lyase has at least one of the following features (1) to (5):

(1) position 108 in the amino acid sequence set forth in SEQ ID NO: 2, or an amino acid corresponding to the position, is methionine, phenylalanine, or valine, (2) position 107 in the amino acid sequence set forth in SEQ ID NO: 2, or an amino acid corresponding to the position, is tryptophan, (3) position 219 in the amino acid sequence set forth in SEQ ID NO: 2, or an amino acid corresponding to the position, is isoleucine, (4) position 223 in the amino acid sequence set forth in SEQ ID NO: 2, or an amino acid corresponding to the position, is isoleucine, (5) position 104 in the amino acid sequence set forth in SEQ ID NO: 2, or an amino acid corresponding to the position, is alanine.

[5] A phenylalanine ammonia lyase variant into which at least one of the following amino acid substitutions (1) to (5) has been introduced:

(1) position 108 in the amino acid sequence set forth in SEQ ID NO: 2, or an amino acid corresponding to the position, is substituted with methionine, phenylalanine, or valine, (2) position 107 in the amino acid sequence set forth in SEQ ID NO: 2, or an amino acid corresponding to the position, is substituted with tryptophan, (3) position 219 in the amino acid sequence set forth in SEQ ID NO: 2, or an amino acid corresponding to the position, is substituted with isoleucine, (4) position 223 in the amino acid sequence set forth in SEQ ID NO: 2, or an amino acid corresponding to the position, is substituted with isoleucine, (5) position 104 in the amino acid sequence set forth in SEQ ID NO: 2, or an amino acid corresponding to the position, is substituted with alanine.

[6]A DNA encoding the phenylalanine ammonia lyase variant according to [5].

[7]A vector including the DNA according to [6].

[8]A host cell into which the DNA according to [6] or the vector according to [7] has been introduced.

[9]A method for producing a phenylalanine ammonia lyase variant, including: culturing the host cell according to [8] and collecting a protein expressed in the host cell.

[10]A method for producing a phenylalanine ammonia lyase variant, including the step of: introducing at least one of the following amino acid substitutions (1) to (5) into a phenylalanine ammonia lyase:

(1) substituting position 108 in the amino acid sequence set forth in SEQ ID NO: 2, or an amino acid corresponding to the position, with methionine, phenylalanine, or valine, (2) substituting position 107 in the amino acid sequence set forth in SEQ ID NO: 2, or an amino acid corresponding to the position, with tryptophan, (3) substituting position 219 in the amino acid sequence set forth in SEQ ID NO: 2, or an amino acid corresponding to the position, with isoleucine, (4) substituting position 223 in the amino acid sequence set forth in SEQ ID NO: 2, or an amino acid corresponding to the position, with isoleucine, (5) substituting position 104 in the amino acid sequence set forth in SEQ ID NO: 2, or an amino acid corresponding to the position, with alanine.

Advantageous Effects of Invention

The present invention makes it possible to provide a method for producing an unsaturated compound having at least two carbon-carbon double bonds using an enzyme. For example, the present invention also makes it possible to produce butadiene using relatively inexpensive L-lysine as a starting material.

BRIEF DESCRIPTION OF DRAWINGS

FIG. 3 shows, with butadiene production quantity when using wild-type PAL set as 1.0, butadiene production quantity when using PAL variant.

DESCRIPTION OF EMBODIMENTS

Figure 1:
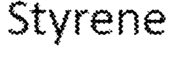
FIG. 1 is a graph showing the results of measuring the amount of styrene produced by adding phenylalanine to a mixed solution of phenylalanine ammonia lyase derived from *Arabidopsis thaliana, Anabaena variabilis*, or *Plagiochasma appendiculatum* (AtPAL, AvPAL, or PaPAL), and ferulic acid decarboxylase.
Figure 1:
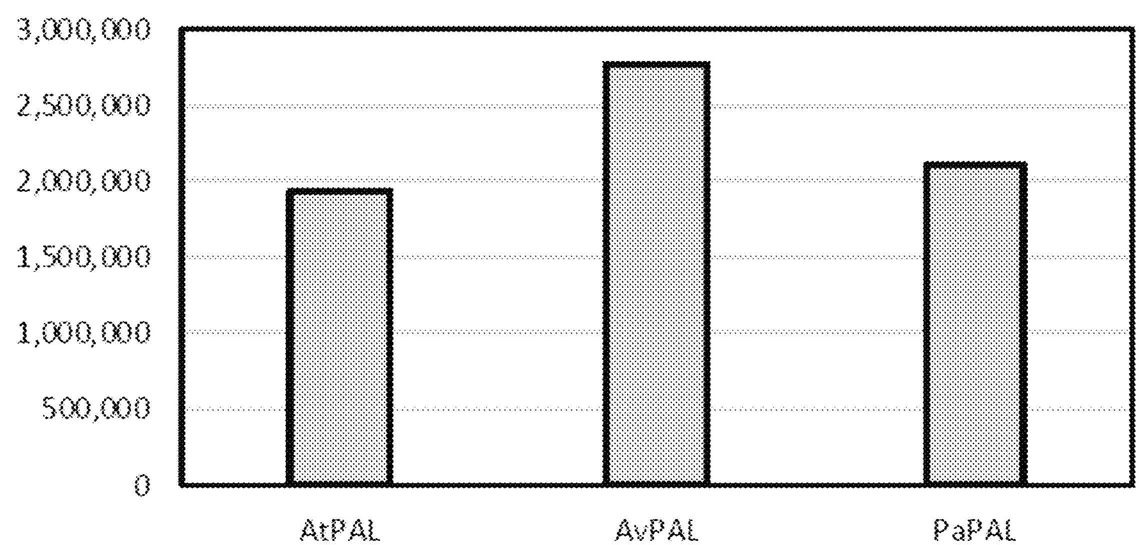

As demonstrated in the following examples, the present inventors have revealed that it is possible to produce unsaturated hydrocarbon compounds, which have carbon-carbon double bonds at both terminuses, such as butadiene, through a three-step reaction using three types of enzymes, as described below.

[Chem. 7]

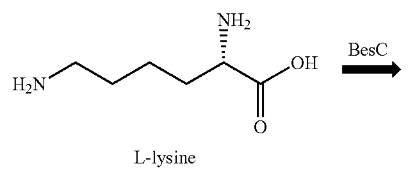

L-lysine

-continued

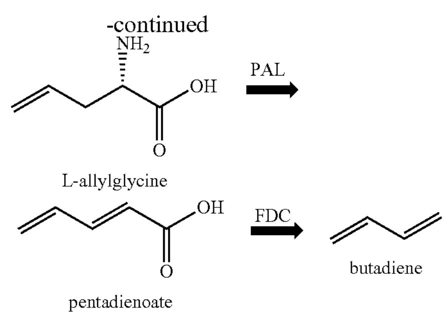

L-allylglycine pentadienoate butadiene

Specifically, the present inventors have revealed that phenylalanine ammonia lyase (PAL) can be used as an enzyme involved in the production of pentadienoate from L-allylglycine.

Therefore, the present invention relates to a method for producing a chain-shaped unsaturated compound having at least two carbon-carbon double bonds, which includes the following reaction step.

[Chem. 8]

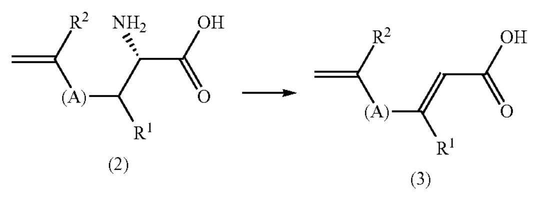
(2) (3)

<Method for Producing Third Chain-Shaped Unsaturated Carboxylic Acid Compound>

As described above, the present invention provides a method for producing a chain-shaped unsaturated carboxylic acid compound or a geometric isomer thereof, represented by the formula (3) (third chain-shaped unsaturated carboxylic acid compound), including the steps of: removing a first amino group from a chain-shaped unsaturated carboxylic acid compound or a geometric isomer thereof, having a first amino group and a first carbon-carbon double bond at a terminus, represented by the formula (2) (second chain-shaped unsaturated carboxylic acid compound), in the presence of phenylalanine ammonia lyase, and forming a second carbon-carbon double bond.

In the present invention, the "third chain-shaped unsaturated carboxylic acid compound" produced in the aforementioned reaction means a chain-shaped unsaturated carboxylic acid compound or a geometric isomer thereof, represented by the formula (3), which has at least two carbon-carbon double bonds, including a carbon-carbon double bond at the terminus.

In the present invention, (A) in each chemical formula represents a linear hydrocarbon group having 0 to 5 carbon atoms, which may be substituted. Note that the term "linear hydrocarbon group having 0 carbon atoms" implies that the carbon atoms bonded via (A) in compounds represented by each chemical formula, as well as geometric isomers thereof, are directly bonded without going through (A). Furthermore, when the number of carbon atoms in the substitutable linear hydrocarbon group is 2 to 5, at least one double bond may be formed between adjacent carbon atoms. In addition, substituents that the hydrocarbon group in (A) may have include, for example, linear or branched alkyl groups having 1 to 5 carbon atoms, linear or branched alkoxy groups having 1 to 5 carbon atoms, hydroxy groups, halogen atoms (such as fluorine, chlorine, bromine, and iodine), nitro groups, cyano groups, amino groups, carboxyl groups, and formyl groups. (A) in each chemical formula is preferably a linear hydrocarbon group having 0 carbon atoms.

In the present invention, $R^1$ and $R^2$ in each chemical formula each independently represent a hydrogen atom, a linear or branched alkyl group having 1 to 5 carbon atoms, a linear or branched alkoxy group having 1 to 5 carbon atoms, or hydroxy group. Examples of the "linear or branched alkyl group having 1 to 5 carbon atoms" include a methyl group, an ethyl group, an n-propyl group, an i-propyl group, an n-butyl group, an i-butyl group, an s-butyl group, a t-butyl group, an n-pentyl group, and an i-pentyl group. Examples of the "linear or branched alkoxy group having 1 to 5 carbon atoms" include a methoxy group, an ethoxy group, an n-propoxy group, an i-propoxy group, an n-butoxy group, an i-butoxy group, an s-butoxy group, a t-butoxy group, an n-pentyloxy group, an i-pentyloxy group, an n-pentyloxy group, and a 1,2-dimethyl-propoxy group. $R^1$ in each chemical formula is preferably a hydrogen atom. $R^2$ is preferably a hydrogen atom or a methyl group.

In each chemical formula, the combinations of (A), $R^1$, and $R^2$ are preferably each a linear hydrocarbon group having zero carbon atoms, a hydrogen group, and a hydrogen group, or a linear hydrocarbon group having zero carbon atoms, a hydrogen group, and a methyl group. Also, in the present invention, the "third chain-shaped unsaturated carboxylic acid compound" is preferably pentadienoate, 4-methylpentadienoate, or 3-methylpentadienoate.

It suffices that the condition of deaminating the second chain-shaped unsaturated carboxylic acid compound in the presence of phenylalanine ammonia lyase according to the present invention is a condition in which the deamination is promoted and a third chain-shaped unsaturated carboxylic acid compound is produced. Those skilled in the art can appropriately adjust and set the composition of the reaction liquid, the pH of the reaction liquid, the reaction temperature, the reaction time, and the like.

For example, the reaction liquid added with the phenylalanine ammonia lyase according to the present invention and its substrate, the second chain-shaped unsaturated carboxylic acid compound, is not particularly limited as long as it does not interfere with the reaction, but preferably a buffer solution having a pH of 6 to 8 and more preferably a buffer solution having a pH of 6 to 7 and containing potassium chloride and sodium phosphate.

In addition, the reaction temperature is not particularly limited either as long as the reaction is not hindered, but is usually 20 to 40° C. and preferably 25 to 37° C. Moreover, the reaction time is not particularly limited as long as it is a time for which the unsaturated hydrocarbon compound can be produced, but is usually 30 minutes to 7 days and preferably 12 hours to 2 days.

In addition, the third chain-shaped unsaturated carboxylic acid compound produced can be collected by appropriately using a known recovery and purification method (such as distillation and chromatography). Moreover, these methods may be carried out alone or may be carried out in multiple steps in appropriate combination.

(Phenylalanine Ammonia Lyase)

The "phenylalanine ammonia lyase" is an enzyme registered as EC number: 4.3.1.24, and means an enzyme which catalyzes a reaction that uses phenylalanine as a substrate to produce cinnamic acid and ammonia. In addition, it is an enzyme also known as PAL, thylases, phenylalanine deaminase, tyrosine ammonia lyase, L-tyrosine ammonia lyase, phenylalanine ammonium lyase, and L-phenylalanine ammonia lyase.

As demonstrated in the following examples, it can be involved in the production of the third chain-shaped unsaturated carboxylic acid compound mentioned earlier, regardless of its origin. Therefore, there are no specific restrictions on the phenylalanine ammonia lyase according to the present invention, and various biologically derived ones can be used. For example, phenylalanine ammonia lyases can come from sources such as *Anabaena variabilis, Arabidopsis thaliana, Plagiochasma appendiculatum, Rhodotorula glutinis, Planctomyces brasiliensis, Oryza sativa, Bambusa oldhamii, Taxus chinensis, Nicotiana tabacum, Streptomyces maritimus, Salvia miltiorrhiza*, and *Solanum lycopersicum*. Among these, the phenylalanine ammonia lyase derived from *Anabaena variabilis* (phenylalanine ammonia lyase composed of the amino acid sequence set forth in SEQ ID NO: 2) is preferable from the viewpoint of having a higher catalytic activity to produce the third chain-shaped unsaturated carboxylic acid compound, as demonstrated in the following examples.

Additionally, the phenylalanine ammonia lyase according to the present invention has identity with the amino acid sequence set forth in SEQ ID NO: 2 by preferably 15% or more (for example, 16% or more, 17% or more, 18% or more, 19% or more), more preferably 20% or more (for example, 30% or more, 40% or more), further preferably 50% or more (for example, 60% or more, 70% or more), more preferably 80% or more (for example, 85% or more, 86% or more, 87% or more, 88% or more, 89% or more), and more preferably 90% or more (for example, 91% or more, 92% or more, 93% or more, 94% or more, 95% or more, 96% or more, 97% or more, 98% or more, 99% or more). Note that the term "identity" to the amino acid sequence set forth in SEQ ID NO: 2 means the proportion (%) of the number of amino acids that matches the amino acid sequence set forth in SEQ ID NO: 2 in the phenylalanine ammonia lyase according to the present invention, based on the total number of amino acids in the phenylalanine ammonia lyase according to the present invention.

Additionally, the phenylalanine ammonia lyase according to the present invention may be one in which mutations have been introduced naturally or unnaturally (artificially) into the amino acid sequence set forth in SEQ ID NO: 2. In other words, the phenylalanine ammonia lyase according to the present invention may also include proteins composed of amino acid sequences in which one or more amino acids in the amino acid sequence of phenylalanine ammonia lyase (such as the amino acid sequence set forth in SEQ ID NO: 2) have been substituted, deleted, added, and/or inserted. The term "more" here implies no particular restriction, but typically it is 2 to 200, preferably 2 to 150, more preferably 2 to 100, further preferably 2 to 70, more preferably 2 to 50, further preferably 2 to 30, more preferably 2 to 20, and further preferably 2 to 10 (for example, 2 to 9, 2 to 8, 2 to 7, 2 to 6, 2 to 5, 2 to 4, 2 or 3, or 2).

Furthermore, as demonstrated in the following examples, the phenylalanine ammonia lyase according to the present invention is preferably a phenylalanine ammonia lyase that has at least one of the following features (1) to (5):

(1) position 108 in the amino acid sequence set forth in SEQ ID NO: 2, or an amino acid corresponding to the position, is methionine, phenylalanine, or valine, (2) position 107 in the amino acid sequence set forth in SEQ ID NO: 2, or an amino acid corresponding to the position, is tryptophan, (3) position 219 in the amino acid sequence set forth in SEQ ID NO: 2, or an amino acid corresponding to the position, is isoleucine, (4) position 223 in the amino acid sequence set forth in SEQ ID NO: 2, or an amino acid corresponding to the position, is isoleucine, (5) position 104 in the amino acid sequence set forth in SEQ ID NO: 2, or an amino acid corresponding to the position, is alanine.

Note that in the present invention, regarding phenylalanine ammonia lyase, the term "corresponding positions" refers to the positions that align with each of leucine at position 108, phenylalanine at position 107, leucine at position 104, leucine at position 219, and asparagine at position 223 in the amino acid sequence set forth in SEQ ID NO: 2. This alignment is achieved when comparing the amino acid sequence set forth in SEQ ID NO: 2 with the amino acid sequences of phenylalanine ammonia lyases and the like from other species, using nucleotide and amino acid sequence analysis software (such as GENETYX-MAC and Sequencher) and BLAST (http://blast.ncbi.nlm.nih.gov/Blast.cgi).

Moreover, in relation to the features (1) to (5), it is preferable to have a phenylalanine ammonia lyase that possesses at least one of the following features: position 108 in the amino acid sequence set forth in SEQ ID NO: 2, or an amino acid corresponding to the position, is methionine; position 107 in the amino acid sequence set forth in SEQ ID NO: 2, or an amino acid corresponding to the position, is tryptophan; and position 108 in the amino acid sequence set forth in SEQ ID NO: 2, or an amino acid corresponding to the position, is phenylalanine. It is more preferable to have a phenylalanine ammonia lyase that possesses at least one of the following features: position 108 in the amino acid sequence set forth in SEQ ID NO: 2, or an amino acid corresponding to the position, is methionine; and position 107 in the amino acid sequence set forth in SEQ ID NO: 2, or an amino acid corresponding to the position, is tryptophan.

Furthermore, the phenylalanine ammonia lyase, which has specific amino acids at such sites, may be a wild type phenylalanine ammonia lyase, and it may also be a mutant phenylalanine ammonia lyase into which amino acid substitution has been introduced so as to have at least one of the features (1) to (5).

Such mutants more specifically include any of the following (a) to (c).

(a) A phenylalanine ammonia lyase mutant including an amino acid sequence in which at least one of the following amino acid substitutions (1) to (5) has been introduced, in the amino acid sequence set forth in SEQ ID NO: 2

(1) position 108 in the amino acid sequence set forth in SEQ ID NO: 2, or an amino acid corresponding to the position, is substituted with methionine, phenylalanine, or valine, (2) position 107 in the amino acid sequence set forth in SEQ ID NO: 2, or an amino acid corresponding to the position, is substituted with tryptophan, (3) position 219 in the amino acid sequence set forth in SEQ ID NO: 2, or an amino acid corresponding to the position, is substituted with isoleucine, (4) position 223 in the amino acid sequence set forth in SEQ ID NO: 2, or an amino acid corresponding to the position, is substituted with isoleucine, (5) position 104 in the amino acid sequence set forth in SEQ ID NO: 2, or an amino acid corresponding to the position, is substituted with alanine.

(b) A phenylalanine ammonia lyase mutant including an amino acid sequence, in the amino acid sequence set forth in SEQ ID NO: 2, where at least one of the amino acid substitutions (1) to (5) has been introduced, and furthermore, one or more amino acids are substituted, deleted, added, and/or inserted at one or several positions other than the aforementioned positions.

(c) A phenylalanine ammonia lyase mutant including an amino acid sequence, which has at least 15% identity with the amino acid sequence set forth in SEQ ID NO: 2, the amino acid sequence having at least one of the following amino acid substitutions (1) to (5) introduced thereto.

The "identity" with the amino acid sequence set forth in SEQ ID NO: 2, of the "more" amino acids that have been substituted, deleted, added, and/or inserted, is as previously described, including their suitable forms (ranges). Additionally, mutants of phenylalanine ammonia lyase may occur naturally or unnaturally (artificially). In other words, this includes phenylalanine ammonia lyase variants where amino acid substitutions and the like have been artificially introduced.

Note that whether phenylalanine ammonia lyase, or natural or non-natural mutants thereof, possess catalytic activity to produce a third chain-shaped unsaturated carboxylic acid compound can be determined by those skilled in the art through known methods (such as chromatography mass spectrometry) by directly measuring the quantity of the unsaturated carboxylic acid compound that is produced.

In addition, the phenylalanine ammonia lyase according to the present invention may be added with additional compounds directly or indirectly. Such addition is not particularly limited, and may be addition at the gene level or chemical addition. Further, the addition position is not particularly limited either, and may be one of the amino terminus and the carboxyl terminus of the phenylalanine ammonia lyase according to the present invention, or may be both of them. The addition at the gene level can be achieved by using a DNA encoding the phenylalanine ammonia lyase according to the present invention, the DNA added with a DNA encoding a different protein with matched reading frames. There is no particular limitation on the "different protein" thus added. For the purpose of facilitating the purification of the phenylalanine ammonia lyase according to the present invention, a tag protein for purification such as polyhistidine (His-) tag protein, FLAG-tag protein (registered trademark, Sigma-Aldrich), or glutathione-S-transferase (GST) is preferably used. In addition, for the purpose of facilitating the detection of the phenylalanine ammonia lyase according to the present invention, a tag protein for detection including a fluorescent protein such as GFP and a chemiluminescent protein such as luciferase is preferably used. The chemical addition may be covalent bond or non-covalent bond. The "covalent bond" is not particularly limited, and examples thereof include an amide bond between an amino group and a carboxyl group, an alkylamine bond between an amino group and an alkyl halide group, a disulfide bond between thiols, and a thioether bond between a thiol group and a maleimide group or an alkyl halide group. Examples of the "non-covalent bond" include a biotin-avidin bond. In addition, as the "additional compounds" thus chemically added, for example, fluorescent dyes such as Cy3 and rhodamine are preferably used for the purpose of facilitating the detection of the phenylalanine ammonia lyase according to the present invention.

In addition, the phenylalanine ammonia lyase according to the present invention may be used by being mixed with additional components. The additional components are not particularly limited, and examples thereof include sterilized water, physiological saline, vegetable oil, surfactants, lipids, solubilizers, buffer agents, protease inhibitors, and preservatives.

<Method for Producing Third Chain-Shaped Unsaturated Carboxylic Acid Compound Through Production of Second Chain-Shaped Unsaturated Carboxylic Acid Compound>

As demonstrated in the following examples, the present inventors have found that the second chain-shaped unsaturated carboxylic acid compound, which serves as a raw material for the production of the aforementioned third chain-shaped unsaturated carboxylic acid compound, can also be produced as shown in the reaction below.

[Chem. 9]

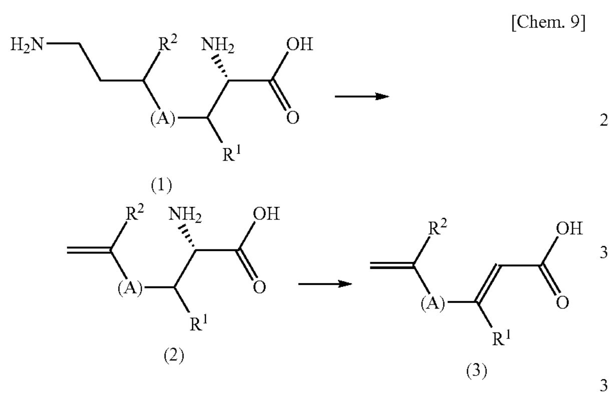

That is, the present inventors have found that it is possible to produce a second chain-shaped unsaturated carboxylic acid compound, represented by the formula (2), by oxidizing the propylamino group at the terminus of the chain-shaped unsaturated carboxylic acid compound or a geometric isomer thereof (the first chain-shaped unsaturated carboxylic acid compound) represented by the formula (1) using the enzyme BesC, thereby cleaving the carbon-carbon bond in the group and forming a carbon-carbon double bond at the terminus. Therefore, the present invention can also take the form of a method for producing a third chain-shaped unsaturated carboxylic acid compound through the production of the second chain-shaped unsaturated carboxylic acid compound.

In the present invention, the "second chain-shaped unsaturated carboxylic acid compound" means a chain-shaped unsaturated carboxylic acid compound or a geometric isomer thereof, as represented by the formula (2), which possesses a first amino group and a first carbon-carbon double bond at the terminus. Furthermore, the "first chain-shaped unsaturated carboxylic acid compound", which serves as a raw material for its production, means a chain-shaped unsaturated carboxylic acid compound or a geometric isomer thereof, as represented by the formula (1), possessing a first amino group and a second amino group at the terminus.

In these compounds, for (A) and $R^1$, including their preferable embodiments, they are as mentioned above, and the "second chain-shaped unsaturated carboxylic acid compound" is preferably L-allylglycine, L-(2-methylallyl)glycine, or L-(3-methylallyl)glycine. The "first chain-shaped unsaturated carboxylic acid compound" is preferably L-lysine, 4-methyllysine, or 3-methyllysine.

It suffices that the condition of forming a carbon-carbon double bond at the terminus of the first chain-shaped unsaturated carboxylic acid compound in the presence of the BesC according to the present invention is a condition in which the formation of the double bond is promoted and a second chain-shaped unsaturated carboxylic acid compound is produced. Those skilled in the art can appropriately adjust and set the composition of the reaction liquid, the pH of the reaction liquid, the reaction temperature, the reaction time, and the like.

For example, the reaction liquid added with the BesC according to the present invention and its substrate, the first chain-shaped unsaturated carboxylic acid compound, is not particularly limited as long as it does not interfere with the reaction, but preferably a buffer solution having a pH of 6 to 8 and more preferably a buffer solution having a pH of 6 to 7 and containing potassium chloride and sodium phosphate. Moreover, from the viewpoint of more easily promoting the reaction, it is preferable to contain iron sulfate.

The reaction temperature is not particularly limited either as long as the reaction is not hindered, but is usually 20 to 40° C. and preferably 25 to 37° C. Moreover, the reaction time is not particularly limited as long as it is a time for which the unsaturated hydrocarbon compound can be produced, but is usually 30 minutes to 7 days and preferably 12 hours to 2 days.

In addition, the second chain-shaped unsaturated carboxylic acid compound produced can be collected by appropriately using a known recovery and purification method (such as distillation and chromatography). Moreover, these methods may be carried out alone or may be carried out in multiple steps in appropriate combination.

Additionally, the first chain-shaped unsaturated carboxylic acid compound, which serves as a raw material, can be purchased as a commercially available product, as demonstrated in the subsequent examples. Furthermore, those skilled in the art could synthesize it while suitably referring to known synthesis methods (such as the method described in the production of L-lysine by fermentation (JP H 0530985 A)).

(BesC)

"BesC" refers to an enzyme involved in β-ethynylserine (Bes) biosynthesis. This enzyme is a terminal alkene-producing enzyme that has an activity to catalyze a reaction that forms a carbon-carbon double bond at the terminus by oxidizing the propylamino group at the terminus to cleave the carbon-carbon bond within this group (NPL 2).

As for the origin of BesC, there are no particular restrictions as long as it has catalytic activity that promotes the production of the second chain-shaped unsaturated carboxylic acid compound, and various biologically derived ones can be used. For example, *Pseudomonas fluorescens* and *Streptomyces cattleya* can be mentioned as sources of BesC. Among these, BesC derived from *Pseudomonas fluorescens* (BesC composed of an amino acid sequence set forth in SEQ ID NO: 11) is preferable.

Additionally, the BesC according to the present invention has identity with the amino acid sequence set forth in SEQ ID NO: 11 by preferably 15% or more (for example, 16% or more, 17% or more, 18% or more, 19% or more), more preferably 20% or more (for example, 30% or more, 40% or more), further preferably 50% or more (for example, 60% or more, 70% or more), more preferably 80% or more (for example, 85% or more, 86% or more, 87% or more, 88% or more, 89% or more), and more preferably 90% or more (for example, 91% or more, 92% or more, 93% or more, 94% or more, 95% or more, 96% or more, 97% or more, 98% or more, 99% or more). Note that the term "identity" to the amino acid sequence set forth in SEQ ID NO: 11 means the proportion (%) of the number of amino acids that matches the amino acid sequence set forth in SEQ ID NO: 11 in the BesC according to the present invention, based on the total number of amino acids in the BesC according to the present invention.

Additionally, the BesC according to the present invention may be one in which mutations have been introduced naturally or unnaturally (artificially) into the amino acid sequence set forth in SEQ ID NO: 11. In other words, the BesC according to the present invention may also include proteins composed of amino acid sequences in which one or more amino acids in the amino acid sequence of BesC (such as the amino acid sequence set forth in SEQ ID NO: 11) have been substituted, deleted, added, and/or inserted. The term "more" here implies no particular restriction, but typically it is 2 to 80, preferably 2 to 70, more preferably 2 to 60, further preferably 2 to 50, more preferably 2 to 40, further preferably 2 to 30, more preferably 2 to 20, and further preferably 2 to 10 (for example, 2 to 9, 2 to 8, 2 to 7, 2 to 6, 2 to 5, 2 to 4, 2 or 3, or 2).

Note that whether BesC, or natural or non-natural mutants thereof, possess catalytic activity to produce a second chain-shaped unsaturated carboxylic acid compound can be determined by those skilled in the art through known methods (such as chromatography mass spectrometry) by directly measuring the quantity of the unsaturated carboxylic acid compound that is produced.

In addition, the BesC according to the present invention may be added with additional compounds directly or indirectly, as with the phenylalanine ammonia lyase according to the present invention described above. Furthermore, the BesC according to the present invention may be used by mixing with other components, as with phenylalanine ammonia lyase.

<Method for Producing Chain-Shaped Unsaturated Hydrocarbon Compound>

As demonstrated in the following examples, the present inventors have found that it is also possible to produce a chain-shaped unsaturated hydrocarbon compound, which has a carbon-carbon double bond at both terminuses, from the above-mentioned third chain-shaped unsaturated carboxylic acid compound.

Specifically, the production method also takes the form indicated below, which includes the steps of producing a third chain-shaped unsaturated carboxylic acid compound, represented by the following formula (3), from the second chain-shaped unsaturated carboxylic acid compound represented by the following formula (2) using phenylalanine ammonia lyase as mentioned above, and producing a chain-shaped unsaturated hydrocarbon compound or a geometric isomer thereof, represented by the following formula (4) (hereinafter simply referred to as a "chain-shaped unsaturated hydrocarbon compound"), from the unsaturated carboxylic acid compound by using ferulic acid decarboxylase to decarboxylate carboxyl groups.

[Chem. 10]

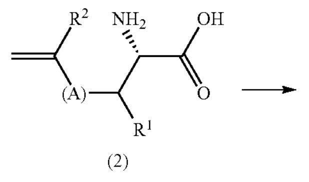

(2)

-continued

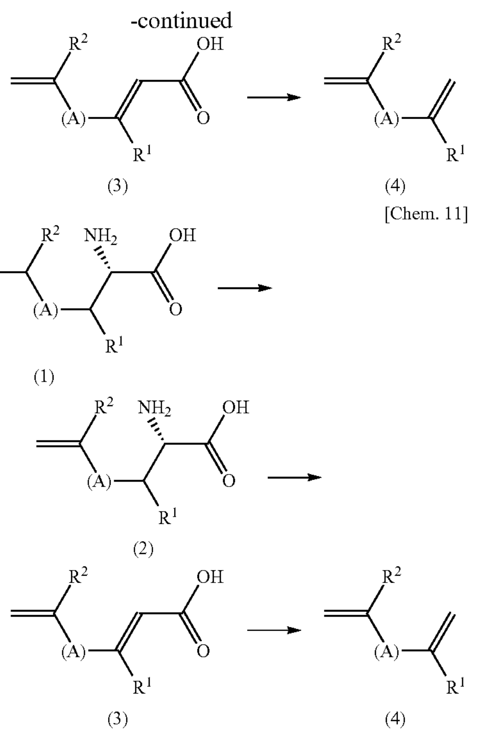

(3) (4)

[Chem. 11]

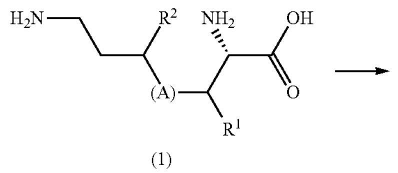

(1)

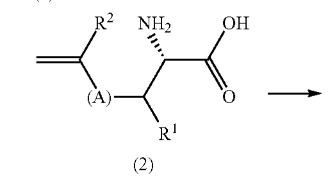

(2)

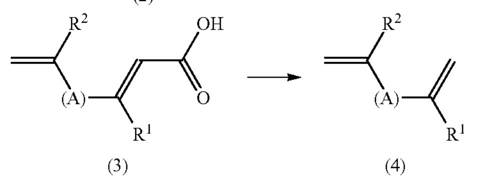

(3) (4)

In the present invention, the "chain-shaped unsaturated hydrocarbon compound" produced in the aforementioned reaction means a chain-shaped unsaturated hydrocarbon compound or a geometric isomer thereof, represented by the formula (4), which has carbon-carbon double bonds at both terminuses.

In the compound, for (A) and $R^1$, including their preferable embodiments, they are as mentioned above, and the "chain-shaped unsaturated hydrocarbon compound" is preferably butadiene and isoprene.

It suffices that the condition of decarboxylating the third chain-shaped unsaturated carboxylic acid compound in the presence of ferulic acid decarboxylase according to the present invention is a condition in which the decarboxylation is promoted and an unsaturated hydrocarbon compound is produced. Those skilled in the art can appropriately adjust and set the composition of the reaction liquid, the pH of the reaction liquid, the reaction temperature, the reaction time, and the like.

For example, the reaction liquid added with the ferulic acid decarboxylase according to the present invention and its substrate, the unsaturated hydrocarbon dicarboxylic acid compound, is not particularly limited as long as it does not interfere with the reaction, but preferably a buffer solution having a pH of 6 to 8 and more preferably a buffer solution having a pH of 6 to 7 and containing potassium chloride and sodium phosphate. Moreover, from the viewpoint of more easily promoting the reaction, it is preferable to contain prenylated flavin mononucleotide (prFMN) or an isomer thereof ($prFMN^{ketimine}$, $prFMN^{iminiu}$, for these prFMN and isomers thereof, see NPL 1).

In addition, the reaction temperature is not particularly limited either as long as the reaction is not hindered, but is usually 20 to 40° C. and preferably 25 to 37° C. Moreover, the reaction time is not particularly limited as long as it is a time for which the unsaturated hydrocarbon compound can be produced, but is usually 30 minutes to 7 days and preferably 12 hours to 2 days.

In addition, the chain-shaped unsaturated hydrocarbon compound produced under such conditions is generally easily vaporized, and thus can be collected by a known volatile gas recovery and purification method. Examples of such collection method include gas stripping, fractional distillation, adsorption, desorption, pervaporation, desorption of unsaturated hydrocarbon compound adsorbed on the solid phase from the solid phase by heat or vacuum, extraction with a solvent, and chromatography (for example, gas chromatography). In addition, when the unsaturated hydrocarbon compound produced is a liquid, it can also be collected by appropriately using a known recovery and purification method (such as distillation and chromatography). Moreover, these methods may be carried out alone or may be carried out in multiple steps in appropriate combination.

(Ferulic Acid Decarboxylase)

The "ferulic acid decarboxylase" is an enzyme registered as EC number: 4.1.1.102, and usually means an enzyme which catalyzes a reaction that decarboxylates ferulic acid to produce 4-vinylguaiacol (4VG).

In the present invention, there are no particular restrictions on the "ferulic acid decarboxylase" as long as it has the activity to catalyze the reaction that removes carboxyl groups from the third chain-shaped unsaturated carboxylic acid compound to produce a chain-shaped unsaturated hydrocarbon compound, and various biologically derived ones can be used. For example, proteins corresponding to "Ferulic acid decarboxylase" on UNIPROT as shown in Tables 1 to 6 of PTLs 3 can be mentioned. Also, as the ferulic acid decarboxylase according to the present invention, preferably *Saccharomyces*-derived ferulic acid decarboxylase and *Aspergillus niger*-derived ferulic acid decarboxylase (UNIPROT ID: A2QHE5 and the like) can be mentioned, more preferably *Saccharomyces*-derived ferulic acid decarboxylase can be mentioned. Note that "*Saccharomyces*" means bacteria belonging to the *Saccharomyces* genus, and examples thereof include *Saccharomyces cerevisiae, Saccharomyces kudriavzevii, Saccharomyces eubayanus, Saccharomyces bayanus, Saccharomyces boulardii, Saccharomyces bulderi, Saccharomyces cariocanus, Saccharomyces cariocus, Saccharomyces chevalieri, Saccharomyces dairenensis, Saccharomyces ellipsoideus, Saccharomyces florentinus, Saccharomyces kluyveri, Saccharomyces martiniae, Saccharomyces monacensis, Saccharomyces norbensis, Saccharomyces paradoxus, Saccharomyces pastorianus, Saccharomyces spencerorum, Saccharomyces turicensis, Saccharomyces unisporus, Saccharomyces uvarum*, and *Saccharomyces zonatus*.

As a ferulic acid decarboxylase derived from *Saccharomyces*, for example, FDC (UNIPROT ID: Q03034, composed of an amino acid sequence set forth in SEQ ID NO: 13) derived from *Saccharomyces cerevisiae* (ATCC 204508/S288c strain) (baker's yeast) can be mentioned, as well as proteins derived from *Saccharomyces* that correspond to "Ferulic acid decarboxylase" on UNIPROT, and more specifically, the ferulic acid decarboxylases shown in Table 1 below can be mentioned. Note that in nature, changes in the nucleotide sequence can cause changes in the amino acid sequence of the protein.

TABLE 1

| Uniprot_ID | Entry Name | Origin |
|---|---|---|
| Q03034 | FDC1_YEAST | Saccharomyces cerevisiae (strain ATCC 204508/8288c) (Baker's yeast) |

TABLE 1-continued

| Uniprot_ID | Entry Name | Origin |
|---|---|---|
| H0GEV9 | H0GEV9_SACCK | Saccharomyces cerevisiae x Saccharomyces kudiayzevii (strain VIN7) |
| E9P8F2 | E9P8F2_YEASX | Saccharomyces cerevisiae |
| E9P8F1 | E9P8F1_YEASX | Saccharomyces cerevisiae |
| A6ZZC4 | A6ZZC4_YEAS7 | Saccharomyces cerevisiae (strain YJM789) |
| N1P7L1 | N1P7L1_YEASC | Saccharomyces cerevisiae strain CEN. PK113-7D |
| H0GPK3 | H0GTK3_SACCK | Saccharomyces cerevisiae x Saccharomyces Kudriavzeyii (strain VIN7) |
| J8TRN5 | JSTRN5_SACK1 | Saccharomyces kudriavzevii (strain ATCC MYA-4449/AS 2.2408/CBS 8840/NBRC 1802/ NCYC 2889) |
| A0A0L8RE03 | A0A0L8RF03_SACEU | Saccharomyces eubayanus |

Additionally, the ferulic acid decarboxylase according to the present invention has identity with the amino acid sequence set forth in SEQ ID NO: 13 by preferably 15% or more (for example, 16% or more, 17% or more, 18% or more, 19% or more), more preferably 20% or more (for example, 30% or more, 40% or more), further preferably 50% or more (for example, 60% or more, 70% or more), more preferably 80% or more (for example, 85% or more, 86% or more, 87% or more, 88% or more, 89% or more), and more preferably 90% or more (for example, 91% or more, 92% or more, 93% or more, 94% or more, 95% or more, 96% or more, 97% or more, 98% or more, 99% or more). Note that the term "identity" to the amino acid sequence set forth in SEQ ID NO: 13 means the proportion (%) of the number of amino acids that matches the amino acid sequence set forth in SEQ ID NO: 13 in the ferulic acid decarboxylase according to the present invention, based on the total number of amino acids in the ferulic acid decarboxylase according to the present invention.

Additionally, the ferulic acid decarboxylase according to the present invention may be one in which mutations have been introduced into the amino acid sequence set forth in SEQ ID NO: 13. In other words, the ferulic acid decarboxylase according to the present invention may also include proteins composed of amino acid sequences in which one or more amino acids in the amino acid sequence of ferulic acid decarboxylase (such as the amino acid sequence set forth in SEQ ID NO: 13) have been substituted, deleted, added, and/or inserted. The term "more" here implies no particular restriction, but typically it is 2 to 150, preferably 2 to 100, more preferably 2 to 80, further preferably 2 to 50, more preferably 2 to 30, further preferably 2 to 20, and more preferably 2 to 10 (for example, 2 to 9, 2 to 8, 2 to 7, 2 to 6, 2 to 5, 2 to 4, 2 or 3, or 2). Additionally, such mutants of ferulic acid decarboxylase may occur naturally or unnaturally (artificially). In other words, this includes ferulic acid decarboxylase variants where amino acid substitutions and the like have been artificially introduced.

Note that whether ferulic acid decarboxylase, or natural or non-natural mutants thereof, possess catalytic activity to produce chain-shaped unsaturated hydrocarbon compounds can be determined by those skilled in the art, for example, as demonstrated in the following examples, by directly measuring the amount of unsaturated hydrocarbon compounds using gas chromatography-mass spectrometry (GC-MS).

In addition, the ferulic acid decarboxylase according to the present invention may be added with additional compounds directly or indirectly, as with the phenylalanine ammonia lyase according to the present invention described above. Furthermore, the ferulic acid decarboxylase according to the present invention may be used by mixing with other components, as with phenylalanine ammonia lyase.

<DNA Encoding Enzyme According to Present Invention and Vector Having the DNA>

Next, an explanation will be given regarding DNA and such that encodes the enzymes according to the present invention (phenylalanine ammonia lyase according to the present invention, BesC according to the present invention, and ferulic acid decarboxylase according to the present invention). By introducing such DNA, it is possible to transform the traits of the host cell, and produce various enzymes according to the present invention in that cell, thus enabling the production of a third chain-shaped unsaturated carboxylic acid compound, or a chain-shaped unsaturated hydrocarbon compound.

The DNA according to the present invention may be, as long as it encodes the above-mentioned enzyme according to the present invention, a natural DNA, a DNA obtained by artificially introducing a mutation into a natural DNA, or a DNA composed of an artificially designed nucleotide sequence. Moreover, the form thereof is not particularly limited, and includes a cDNA as well as a genomic DNA and a chemically synthesized DNA. These DNAs can be prepared by those skilled in the art using conventional means. The genomic DNA can be prepared, for example, as follows. Specifically, a genomic DNA is extracted from various bacteria to create a genomic library (as a vector, plasmid, phage, cosmid, BAC, PAC, or the like can be used). This is developed, and colony hybridization or plaque hybridization is performed using a probe prepared based on the nucleotide sequence of the gene encoding the enzyme according to the present invention (for example, the nucleotide sequence set forth in SEQ ID NO: 1). In addition, it is also possible to prepare a genomic DNA by preparing a primer specific to the gene encoding the enzyme according to the present invention and performing PCR using this primer. In addition, a cDNA can be prepared, for example, as follows. Specifically, an mRNA extracted from various bacteria is used as a basis to synthesize a cDNA, which is inserted into a vector such as AZAP to prepare a cDNA library. This is developed, and colony hybridization or plaque hybridization, or PCR is performed in the same manner as described above.

Then, those skilled in the art can introduce, if necessary, a mutation encoding the above-mentioned amino acid substitution into the DNA thus prepared by using a known site-specific mutagenesis. Examples of site-specific mutagenesis include the Kunkel method (Kunkel, T. A., Proc Natl Acad Sci USA, 1985, Volume 82, issue 2, pages 488 to 492) and the SOE (splicing-by-overlap-extension)-PCR method (Ho, S. N., Hunt, H. D., Horton, R. M., Pullen, J. K., and Pease, L. R., Gene, 1989, Volume 77, pages 51 to 59).

In addition, those skilled in the art can artificially design a nucleotide sequence encoding a protein in which the above-mentioned amino acid substitution has been introduced, and use an automatic nucleic acid synthesizer based on the sequence information to chemically synthesize the DNA according to the present invention.

Moreover, from the viewpoint of further improving the expression efficiency of the encoded decarboxylase according to the present invention in the host cell, the DNA according to the present invention may can the form of a DNA encoding the enzyme according to the present invention in which the codon is optimized in accordance with the type of the host cell.

In addition, in order to make it possible to replicate the above-mentioned DNA in the host cell, the present invention can take the form of a vector inserted with the DNA.

In the present invention, the "vector" can be constructed based on, for example, a plasmid, which exists as a self-replicating vector, that is, an extrachromosomal independent entity whose replication is independent of chromosomal replication. In addition, a vector may be one that, when introduced into a host cell, is integrated into the genome of the host cell and replicated together with the chromosome into which it has been integrated.

Examples of such vector include plasmids and phage DNAs. In addition, examples of the plasmids include plasmids derived from *E. coli* (such as pET22, pBR322, pBR325, pUC118, pUC119, pUC18, and pUC19), plasmids derived from yeast (such as YEp13, YEp24, and YCp50), and plasmids derived from *Bacillus subtilis* (such as pUB110 and pTP5). Examples of the phage DNAs include λ phages (such as Charon4A, Charon21A, EMBL3, EMBL4, λgt10, λgt11, and λZAP). Furthermore, as a vector according to the present invention, an insect virus vector such as a baculovirus can be used when the host cell is derived from an insect, T-DNA or the like can be used when the host cell is derived from a plant, and an animal virus vector such as a retrovirus or an adenovirus vector can also be used when the host cell is derived from an animal. In addition, as a vector construction procedure and method according to the present invention, ones conventionally used in the field of genetic engineering can be used. For example, in order to insert the DNA according to the present invention into a vector, a method is employed in which a purified DNA is first cleaved with an appropriate restriction enzyme, inserted into a restriction enzyme site or a multicloning site of an appropriate vector, and ligated to the vector.

In addition, the vector according to the present invention may be in the form of an expression vector containing the enzyme according to the present invention encoded by the DNA in a state capable of expression in a host cell. For the purpose of introduction into a host cell to express the enzyme according to the present invention, the "expression vector" according to the present invention preferably contains, in addition to the DNA, a DNA sequence for controlling the expression, a genetic marker for selecting a transformed host cell, and the like. Examples of the DNA sequence for controlling expression include promoters, enhancers, splicing signals, poly A addition signals, ribosome binding sequences (SD sequences), and terminators. The promoters are not particularly limited as long as they exhibit transcriptional activity in the host cell, and can be obtained as a DNA sequence which controls the expression of a gene encoding a protein that is of a type same as or different from the host cell. In addition to the DNA sequence which controls expression, a DNA sequence which induces expression may be contained. When the host cell is a bacterium, examples of such DNA sequence which induces expression include the lactose operon, which can induce expression of a gene located downstream by the addition of isopropyl-β-D-thiogalactopyranoside (IPTG). The gene marker in the present invention may be appropriately selected according to the method of selecting a transformed host cell. For example, it is possible to use a gene encoding drug resistance and a gene complementary to auxotrophy.

The vector may be inserted with a single type of DNA encoding the enzyme according to the present invention, and it is also possible to insert multiple types of DNA into one vector. In the case of inserting multiple types of DNA into a vector, when multiple types of DNA are inserted into one vector, it is preferable for these DNAs to form an operon. Here, "operon" refers to a nucleic acid sequence unit composed of one or more genes transcribed under the control of the same promoter.

In the present invention, examples of such vectors include the following:

- a vector into which the DNA encoding the phenylalanine ammonia lyase according to the present invention has been inserted,
- a combination of a vector into which the DNA encoding the BesC according to the present invention has been inserted, and a vector into which the DNA encoding the phenylalanine ammonia lyase according to the present invention has been inserted,
- a combination of a vector into which the DNA encoding the phenylalanine ammonia lyase according to the present invention has been inserted, and a vector into which the DNA encoding the ferulic acid decarboxylase according to the present invention has been inserted, or
- a combination of a vector into which the DNA encoding the BesC according to the present invention has been inserted, a vector into which the DNA encoding the phenylalanine ammonia lyase according to the present invention has been inserted, and a vector into which the DNA encoding the ferulic acid decarboxylase according to the present invention has been inserted.

In addition, it is also possible to mention the following:

- a vector into which the DNA encoding the BesC according to the present invention and the DNA encoding the phenylalanine ammonia lyase according to the present invention have been inserted,
- a vector into which the DNA encoding the phenylalanine ammonia lyase according to the present invention and the ferulic acid decarboxylase according to the present invention have been inserted, or
- a vector into which the DNA encoding the BesC according to the present invention, the DNA encoding the phenylalanine ammonia lyase according to the present invention and the ferulic acid decarboxylase according to the present invention have been inserted.

In addition, the DNA or vector according to the present invention may be used by being mixed with additional components. The additional components are not particularly limited, and examples thereof include sterilized water, physiological saline, vegetable oil, surfactants, lipids, solubilizers, buffer agents, DNase inhibitors, and preservatives.

<Agent for Promoting Production of Third Chain-Shaped Unsaturated Carboxylic Acid Compound or Chain-Shaped Unsaturated Hydrocarbon Compound>

As described above, it becomes possible to facilitate the production of the third chain-shaped unsaturated carboxylic acid compound, or chain-shaped unsaturated hydrocarbon compounds, by using the enzyme according to the present invention, the DNA encoding this enzyme, or the vector into which this DNA has been inserted.

Therefore, the present invention provides an agent for promoting the production of a third chain-shaped unsaturated carboxylic acid compound or a chain-shaped unsaturated hydrocarbon compound, comprising an enzyme according to the present invention, a DNA encoding the enzyme, or a vector into which the DNA has been inserted.

More specifically, the following embodiments can be mentioned:

- an agent for promoting the production of a third chain-shaped unsaturated carboxylic acid compound from a second chain-shaped unsaturated carboxylic acid compound, comprising the phenylalanine ammonia lyase according to the present invention, a DNA encoding the enzyme, or a vector into which the DNA has been inserted,
- an agent for promoting the production of a third chain-shaped unsaturated carboxylic acid compound from a first chain-shaped unsaturated carboxylic acid compound, comprising the BesC according to the present invention, a DNA encoding the enzyme, or a vector into which the DNA has been inserted, and the phenylalanine ammonia lyase according to the present invention, a DNA encoding the enzyme, or a vector into which the DNA has been inserted,
- an agent for promoting the production of a third chain-shaped unsaturated carboxylic acid compound from a first chain-shaped unsaturated carboxylic acid compound, comprising a vector into which a DNA encoding the BesC according to the present invention and a DNA encoding the phenylalanine ammonia lyase according to the present invention have been inserted,
- an agent for promoting the production of a chain-shaped unsaturated hydrocarbon compound from a second chain-shaped unsaturated carboxylic acid compound, comprising:

the phenylalanine ammonia lyase according to the present invention, a DNA encoding the enzyme, or a vector into which the DNA has been inserted; and the ferulic acid decarboxylase according to the present invention, a DNA encoding the enzyme, or a vector into which the DNA has been inserted,

- an agent for promoting the production of a chain-shaped unsaturated hydrocarbon compound from a second chain-shaped unsaturated carboxylic acid compound, comprising a vector into which a DNA encoding the phenylalanine ammonia lyase according to the present invention and a DNA encoding the ferulic acid decarboxylase according to the present invention have been inserted,
- an agent for promoting the production of a chain-shaped unsaturated hydrocarbon compound from a first chain-shaped unsaturated carboxylic acid compound, comprising:

the BesC according to the present invention, a DNA encoding the enzyme or a vector into which the DNA has been inserted; the phenylalanine ammonia lyase according to the present invention, a DNA encoding the enzyme or a vector into which the DNA has been inserted; and the ferulic acid decarboxylase according to the present invention, a DNA encoding the enzyme or a vector into which the DNA has been inserted,

- an agent for promoting the production of a chain-shaped unsaturated hydrocarbon compound from a first chain-shaped unsaturated carboxylic acid compound, comprising a vector into which a DNA encoding the BesC according to the present invention, a DNA encoding the phenylalanine ammonia lyase according to the present invention and a DNA encoding the ferulic acid decarboxylase according to the present invention have been inserted.

Such an agent may be one containing the enzyme according to the present invention or the like, or may be used by being mixed with additional components. Such additional components are not particularly limited, and examples thereof include sterilized water, physiological saline, vegetable oil, surfactants, lipids, solubilizers, buffer agents, protease inhibitors, DNase inhibitors, and preservatives.

The present invention can also provide a kit including such an agent. In the kit of the present invention, the agent may be included in the form of a host cell described later into which the DNA or the like according to the present invention has been introduced and transformed. Moreover, in addition to such an agent, the kit of the present invention may include various substrates (the first chain-shaped unsaturated carboxylic acid compound and the second chain-shaped unsaturated carboxylic acid compound), a host cell for introducing the DNA or the like according to the present invention, a medium for culturing the host cell, an instruction manual for use thereof, and the like. Moreover, such an instruction manual is a manual for using the agent of the present invention and the like in the method for producing the above-mentioned third chain-shaped unsaturated carboxylic acid compound or chain-shaped unsaturated hydrocarbon compound. The manual can include, for example, information on the experimental method and experimental conditions for the production method of the present invention, the agent of the present invention, and the like (for example, information such as a vector map showing the nucleotide sequence of a vector, sequence information on the enzyme according to the present invention, information on the origin and properties of the host cell as well as the culture conditions of the host cell, and the like).

<Host Cell Introduced with DNA Encoding Enzyme According to Present Invention, and the Like>

Next, description is provided for a host cell introduced with the DNA or vector according to the present invention. Use of a host cell transformed by the introduction of the above-mentioned DNA or vector makes it possible to produce the enzyme according to the present invention, and makes it possible to further produce the third chain-shaped unsaturated carboxylic acid compound or chain-shaped unsaturated hydrocarbon compound.

The host cell introduced with the DNA or vector according to the present invention is not particularly limited, and examples thereof include microorganisms (such as *E. coli*, budding yeast, fission yeast, *Bacillus subtilis*, actinomycetes, and filamentous fungi), plant cells, insect cells, and animal cells. However, it is preferable to use a microorganism, and it is more preferable to use *E. coli* as a host cell from the viewpoint that it is possible to contribute to the production of the third chain-shaped unsaturated carboxylic acid compound or chain-shaped unsaturated hydrocarbon compound with a relatively inexpensive medium, with high proliferation properties in a short time, and further with high productivity.

In addition, the host cell introduced with the DNA or vector according to the present invention is preferably a cell which retains a flavin prenyltransferase from the viewpoint of inducing prenylation of flavin mononucleotide (FMN) and producing prFMN or an isomer thereof which contributes to improving the productivity of the chain-shaped unsaturated hydrocarbon compound.

In addition, the host cell introduced with the DNA or vector according to the present invention is preferably *E. coli* C41 (DE3) cells because they are easy to handle and can express toxic proteins.

The introduction of the DNA or vector according to the present invention can be carried out according to a method conventionally used in this field. Examples of the method for introduction into microorganisms such as *E. coli* include the heat shock method, the electroporation method, the spheroplast method, and the lithium acetate method, examples of the method for introduction into plant cells include a method using *Agrobacterium* and the particle gun method, examples of the method for introduction into insect cells include a method using baculovirus and the electroporation method, and examples of the method for introduction into animal cells include the calcium phosphate method, the lipofection method, and the electroporation method.

The DNA or the like thus introduced into the host cell may be, in the host cell, retained by being randomly inserted into its genomic DNA, may be retained by homologous recombination, and can be, in the case of a vector, replicated and retained as an independent entity outside the genomic DNA.

<Method for Producing Third Chain-Shaped Unsaturated Carboxylic Acid Compound or Chain-Shaped Unsaturated Hydrocarbon Compound Using Host Cell>

As described above, by cultivating a host cell that has been transformed to express an enzyme according to the present invention, it is possible to produce a third chain-shaped unsaturated carboxylic acid compound or chain-shaped unsaturated hydrocarbon compound. Therefore, the present invention also provides a method for producing a third chain-shaped unsaturated carboxylic acid compound or chain-shaped unsaturated hydrocarbon compound, including the steps of cultivating a host cell into which a DNA or vector encoding an enzyme according to the present invention has been introduced, and collecting the third chain-shaped unsaturated carboxylic acid compound or chain-shaped unsaturated hydrocarbon compound that has been produced in the host cell and/or a culture thereof.

"The host cell that has been transformed to express an enzyme according to the present invention" is as described above. Furthermore, in such host cells, the combination of the enzyme according to the present invention to be expressed or retained, the DNA encoding the enzyme, and the vector into which the DNA has been inserted, can be subjected to appropriate design changes by those skilled in the art in consideration of the combination of starting materials (substrates) and final products based on the examples shown in the aforementioned <DNA Encoding Enzyme According to Present Invention and Vector Having the DNA> and <Agent for Promoting Production of Third Chain-Shaped Unsaturated Carboxylic Acid Compound or Chain-Shaped Unsaturated Hydrocarbon Compound>.

The culture conditions for the cell are as described later, and the medium is preferably added with various substrates (the first chain-shaped unsaturated carboxylic acid compound and the second chain-shaped unsaturated carboxylic acid compound). The culture temperature can be appropriately changed according to the type of the host cell to be used, but is usually 20 to 40° C. and preferably 25 to 37° C.

In the present invention, the "culture" is a medium containing proliferated host cells, secreted products of the host cells, metabolites of the host cells, and the like obtained by culturing the host cells in a medium, and includes dilutions and concentrates thereof. The collection of a third chain-shaped unsaturated carboxylic acid compound or chain-shaped unsaturated hydrocarbon compound from such host cell and/or culture is not particularly limited either, and can be performed using the above-described known recovery and purification methods. In addition, the time period of collection is appropriately adjusted according to the type of the host cell to be used, and may be any time which can produce a third chain-shaped unsaturated carboxylic acid compound or chain-shaped unsaturated hydrocarbon compound, but is usually 30 minutes to 7 days and preferably 12 hours to 2 days.

<Method for Producing Phenylalanine Ammonia Lyase Variant According to Present Invention>

As presented in Examples to be described later, culturing of a host cell introduced with a DNA or the like encoding the phenylalanine ammonia lyase variant according to the present invention makes it possible to produce the variant in the host cell.

Therefore, the present invention can provide a method for producing a phenylalanine ammonia lyase variant, including culturing a host cell introduced with a DNA encoding the phenylalanine ammonia lyase variant according to the present invention or a vector containing the DNA, and collecting a protein expressed in the host cell.

In the present invention, the conditions for "culturing a host cell" may be any conditions as long as the host cell can produce the phenylalanine ammonia lyase variant according to the present invention, and according to the type of the host cell, the medium used, and the like, those skilled in the art can appropriately adjust and set the temperature, the presence or absence of addition of air, the concentration of oxygen, the concentration of carbon dioxide, the pH of the medium, the culture temperature, the culture time, the humidity, and the like.

Such a medium only needs to have a content which can be used as a nutrient source by the host cell, and examples of the content include carbon sources, nitrogen sources, sulfur sources, inorganic salts, metals, peptones, yeast extracts, meat extracts, casein hydrolysates, and serum. In addition, such a medium may be added with, for example, IPTG for inducing the expression of a DNA encoding the phenylalanine ammonia lyase variant according to the present invention, an antibiotic corresponding to the drug resistance gene which can be encoded by the vector according to the present invention (for example, ampicillin), or a nutrient corresponding to a gene complementing the auxotrophy which can be encoded by the vector according to the present invention (for example, arginine or histidine).

Additionally, examples of the method for "collecting a protein expressed in the host cell" from the host cell thus cultured include a method in which the host cell is recovered from the medium by filtration, centrifugation, or the like, the recovered host cell is treated by cell lysis, grinding treatment, or pressure crushing, and further, the protein expressed in the host cell is purified and concentrated by ultrafiltration treatment, salting out, solvent precipitation such as ammonium sulfate precipitation, chromatography (such as gel chromatography, ion exchange chromatography, or affinity chromatography), or the like. Moreover, when the phenylalanine ammonia lyase variant according to the present invention is added with the above-mentioned purified tag protein, it can be purified and collected using a substrate to which the tag protein is adsorbed. Moreover, these purification and concentration methods may be carried out alone or may be carried out in multiple steps in appropriate combination.

In addition, the phenylalanine ammonia lyase variant according to the present invention is not limited to the above-described biological synthesis, and can also be produced using the DNA or the like according to the present invention and a cell-free protein synthesis system. Such a cell-free protein synthesis system is not particularly limited, and examples thereof include synthesis systems derived from wheat germ, *E. coli*, rabbit reticulocytes, and insect cells. Moreover, those skilled in the art can chemically synthesize the phenylalanine ammonia lyase variant according to the present invention using a commercially available peptide synthesizer or the like.

In addition, the present invention provides a method for producing a phenylalanine ammonia lyase variant with enhanced catalytic activity to produce a third chain-shaped unsaturated carboxylic acid compound from a second chain-shaped unsaturated carboxylic acid compound, the production method including introducing at least one of the following amino acid substitutions (1) to (5) in phenylalanine ammonia lyase:

(1) substituting position 108 in the amino acid sequence set forth in SEQ ID NO: 2, or an amino acid corresponding to the position, with methionine, phenylalanine, or valine, (2) substituting position 107 in the amino acid sequence set forth in SEQ ID NO: 2, or an amino acid corresponding to the position, with tryptophan, (3) substituting position 219 in the amino acid sequence set forth in SEQ ID NO: 2, or an amino acid corresponding to the position, with isoleucine, (4) substituting position 223 in the amino acid sequence set forth in SEQ ID NO: 2, or an amino acid corresponding to the position, with isoleucine, (5) substituting position 104 in the amino acid sequence set forth in SEQ ID NO: 2, or an amino acid corresponding to the position, with alanine.

The term "phenylalanine ammonia lyase variant with enhanced catalytic activity to produce a third chain-shaped unsaturated carboxylic acid compound from a second chain-shaped unsaturated carboxylic acid compound" means phenylalanine ammonia lyase with higher catalytic activity to produce a third chain-shaped unsaturated carboxylic acid compound compared to before the introduction of the amino acid substitution, and the comparison target typically includes various phenylalanine ammonia lyases derived from different organisms and natural mutants thereof.

The introduction of "amino acid substitution" in phenylalanine ammonia lyase can be accomplished by modifying the DNA that encodes it. Such "DNA modification" can be appropriately carried out, as mentioned above, by those skilled in the art using well-known methods such as site-specific mutagenesis and chemical synthesis of DNA based on modified sequence information. Additionally, the introduction of "amino acid substitution" can also be carried out using the chemical synthesis of peptides as described above.

Whether the introduction of such amino acid substitution enhances the catalytic activity for the production of olefin compounds can be assessed, as mentioned earlier, by chromatography mass spectrometry, and other methods. Moreover, phenylalanine ammonia lyase variants produced in this manner have a catalytic activity to produce a third chain-shaped unsaturated carboxylic acid compound, which is preferably 1.2 times or more (1.3 times or more, 1.4 times or more, 1.5 times or more, 1.6 times or more, 1.7 times or more, 1.8 times or more, 1.9 times or more), more preferably 2 times or more, further preferably 3 times or more, more preferably 4 times or more, and further preferably 5 times or more or more, as compared to the phenylalanine ammonia lyase composed of the amino acid sequence set forth in SEQ ID NO: 2.

EXAMPLES

Hereinafter, the present invention is described more specifically based on Examples, but the present invention is not limited to the following Examples.

The present inventors envisioned the following reaction scheme to produce butadiene with L-lysine as a starting material in a three-step reaction using three enzymes (BesC, PAL, FDC).

[Chem. 12]

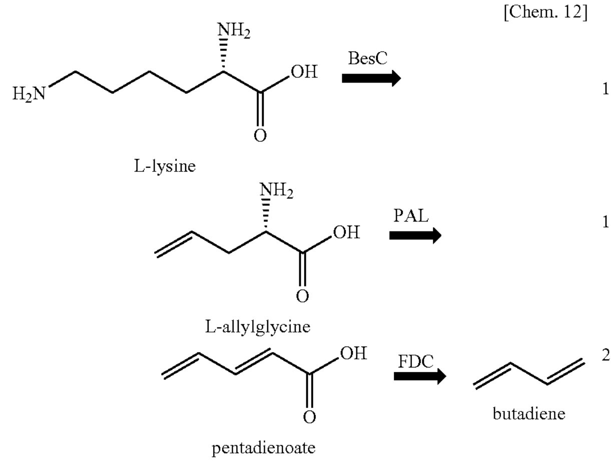

Therefore, a demonstration experiment was carried out for this reaction scheme as follows.

Example 1

<Preparation of Plasmid Vector>

First, in order to efficiently express BesC derived from *Pseudomonas fluorescens*, PAL derived from *Arabidopsis thaliana*, and FDC derived from *Saccharomyces cerevisiae* in *E. coli*, the frequency of codon usage in *E. coli* was considered to perform modification, thereby designing a nucleotide sequence. Subsequently, a DNA composed of such a modified nucleotide sequence was chemically synthesized according to a conventional method. Then, the DNA thus prepared and the pET22b(+) vector (manufactured by Novagen) were ligated by the Gibson Assembly method (using a kit of New England Biolabs, NEBuilder HiFi DNA Assembly Master Mix (registered trademark)), to thereby prepare plasmid vectors (BesC vector, PAL vector, FDC vector 1) capable of expressing the various wild type genes in *E. coli*. Similarly, the pColADuet vector (manufactured by Novagen) and a DNA obtained by amplifying a gene (SEQ ID NO: 15) encoding flavin prenyltransferase (hereinafter also referred to as "UbiX") from *E. coli* (K-12) strain by the PCR method were ligated by the Gibson Assembly method, to thereby prepare a plasmid vector (UbiX vector) capable of expressing the wild type UbiX in *E. coli*.

Note that for the amino acid sequences of the enzymes used in Example 1 and the subsequent Example 2, and the DNA sequences encoding them (wild type sequences, sequences modified considering the codon usage frequency in *E. coli*), refer to the sequences set forth in the SEQ ID NOs shown in Table 2 below.

TABLE 2

| | Amino Acid Sequence | Wild Type DNA Sequence | DNA Sequence with Optimized Codon |
|---|---|---|---|
| AvPAL | SEQ ID NO: 2 | SEQ ID NO: 1 | SEQ ID NO: 3 |
| PaPaL | SEQ ID NO: 5 | SEQ ID NO: 4 | SEQ ID NO: 6 |
| AtPAL | SEO ID NO: 8 | SEQ ID NO: 7 | SEQ ID NO: 9 |

TABLE 2-continued

| | Amino Acid Sequence | Wild Type DNA Sequence | DNA Sequence with Optimized Codon |
|---|---|---|---|
| PfBesC | SEQ ID NO: 11 | — | SEQ ID NO: 10 |
| ScFDC | SEQ ID NO: 13 | SEQ ID NO: 12 | SEQ ID NO: 14 |
| UbiX | SEQ ID NO: 16 | SEQ ID NO: 15 | — |

<Preparation of Enzyme Expression Medium and Measurement of Enzyme Activity>

The vectors prepared as described above (5 μg of BesC vector or 5 μg of PAL vector) were introduced into *E. coli* C41 (DE3) strain (manufactured by Lucigen Corporation, 100 μL) by the heat shock method to prepare transformants expressing wild type BesC or PAL. Then, each of these transformants was cultured for 6 hours in an LB medium supplemented with ampicillin. It should be noted that the growth of these transformants reaches a peak after such 6-hour culture (pre-culture). For this reason, the amount of bacterial cells at the start of the enzyme reaction to be described later is uniform among these transformants.

In addition, addition was carried out to achieve 12 g/L tryptone, 24 g/L yeast extract, 10 g/L glycerol, 9.4 g/L dipotassium hydrogen phosphate, 2.2 g/L potassium dihydrogen phosphate, 20 g/L lactose, and 100 mg/L ampicillin, to thereby prepare an enzyme expression medium.

In a 500 mL baffled triangular flask, 1 mL of the aforementioned *E. coli* culture fluid that had been cultivated for 6 hours, and 100 mL of the aforementioned enzyme expression medium were added, followed by further cultivation at 37° C. and a shaking rate of 180 rpm for an additional 18 hours. After cultivation, the culture medium was centrifuged at 5,000 rpm for 10 minutes, and after the supernatant was removed, 10 mL of protein extraction solution B-PER™ Bacterial Cell Lysis Reagent (Thermo Fisher Scientific) was added to suspend the pellet. After shaking it at a permeation speed of 60 rpm in an ice bath, the various cell lysates were prepared by centrifuging it at 15,000 rpm for 15 minutes.

Similarly, the prepared vectors (5 μg of FDC vector 1 and 5 μg of UbiX vector) were introduced into *E. coli* C41 (DE3) strain (manufactured by Lucigen Corporation, 100 μL) by the heat shock method to prepare transformants co-expressing wild type FDC and UbiX. They were cultured for 6 hours in LB medium supplemented with ampicillin and kanamycin. The above enzyme reaction medium supplemented with 50 mg/L kanamycin was prepared, and a cell lysate was prepared in the same manner.

Then, to a 10 mL vial for a headspace type gas chromatography mass spectrometer (HS/GSMS), 100 μL each of the various cell lysates, 100 μL of 1 M phosphate buffer solution (pH 6.8), L-lysine to a final concentration of 10 mM, and ultrapure water to 1 mL were added. Immediately after that, the cap of the vial was closed, followed by enzyme reaction at 37° C. and a shaking rate of 180 rpm. The peak areas representing the amount of 1,3-butadiene produced in the headspace of the vial 18 hours after the start of the reaction were measured by GC-MS (manufactured by Shimadzu Corporation under the trade name: GCMS-QP Ultra).

As a result, although not shown in the figure, butadiene was not detected without the addition of L-lysine, but the production of 1,3-butadiene was confirmed with the addition of L-lysine.

Example 2

As shown in Example 1, the combination of various wild type enzymes was observed to produce butadiene from L-lysine. Therefore, in order to further improve this catalytic activity, PALs derived from other hosts were examined for the PALs that perform the second step in the reaction.

<Preparation of Plasmid Vector>

In order to efficiently express PAL derived from *Anabaena variabilis* or *Plagiochasma appendiculatum* in *E. coli*, the frequency of codon usage in *E. coli* was considered to perform modification, thereby designing a nucleotide sequence. Subsequently, a DNA composed of such a modified nucleotide sequence was chemically synthesized according to a conventional method, to thereby prepare plasmid vectors (various PAL vectors) capable of expressing the various wild type genes in *E. coli*, as in the same manner as above.

Subsequently, the pZA33luc vector (manufactured by Expressys) and a DNA obtained by amplifying FDC vector 1 and pTrcHis B vector (Thermo Fisher Scientific) by the PCRmethod were ligated by the Gibson Assembly method, to thereby prepare an FDC plasmid vector (FDC vector 2) for enzyme activity measurement in *E. coli.*

<Preparation of Enzyme Activity Measurement Medium and Measurement of Enzyme Activity>

The prepared vectors (5 μg of PAL vector, 5 μg of UbiX vector, and 5 μg of FDC vector 2) were introduced into *E. coli* C41 (DE3) strain (manufactured by Lucigen Corporation, 100 μL) by the heat shock method to prepare a transformant co-expressing various PALs and wild type FDC and UbiX.

Then, each of these transformants was cultured for 6 hours in an LB medium supplemented with ampicillin, kanamycin, and chloramphenicol. It should be noted that the growth of these transformants reaches a peak after such 6-hour culture (pre-culture). For this reason, the amount of bacterial cells at the start of the enzyme reaction to be described later is uniform among these transformants.

Further, in addition to 12 g/L tryptone, 24 g/L yeast extract, 10 g/L glycerol, 9.4 g/L dipotassium hydrogen phosphate, 2.2 g/L potassium dihydrogen phosphate, 20 g/L lactose, 100 mg/L ampicillin, 50 mg/L kanamycin, and 30 mg/L chloramphenicol, 1 mM phenylalanine or 1 mM allylglycine was added as a substrate to prepare an enzyme activity measurement medium.

Then, to a 10 mL vial for HS/GSMS, 50 μL of culture solution of the aforementioned transformants and 1 mL of enzyme activity measurement medium were added, and immediately after that, the cap of the vial was closed, followed by enzyme reaction at 37° C. and a shaking rate of 180 rpm. The peak areas representing the amount of styrene or 1,3-butadiene produced in the headspace of the vial 18 hours after the start of the reaction were measured by GC-MS.

As a result, as shown in FIG. 1, when phenylalanine was added as a substrate, styrene production was observed for all PALs, as indicated below. Moreover, no significant difference was seen in its amount produced between the three types of PALs.

Figure 2:
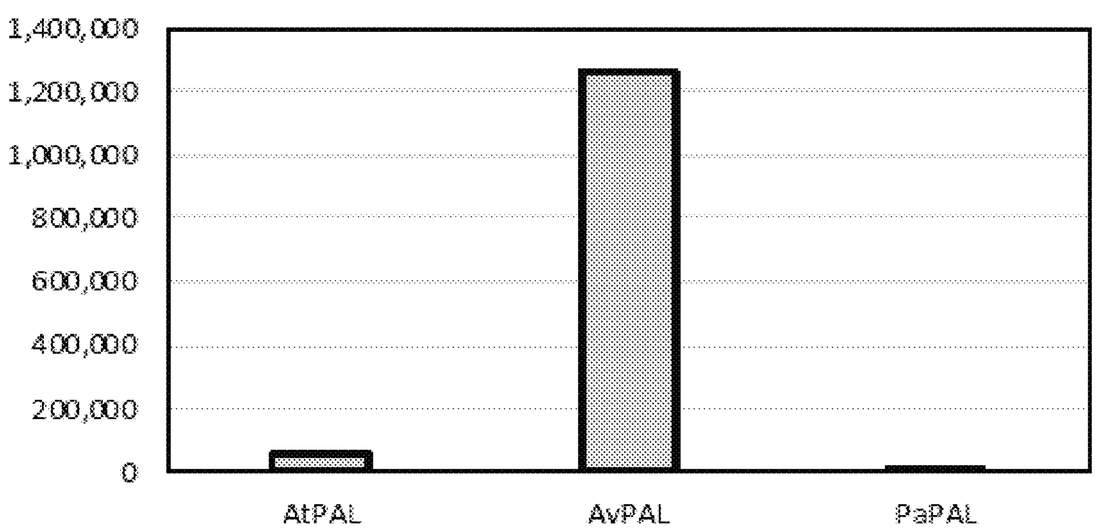
FIG. 2 is a graph showing the results of measuring the amount of butadiene produced by adding allylglycine to a mixed solution of AtPAL, AvPAL, or PaPAL and ferulic acid decarboxylase.

On the other hand, as shown in FIG. 2, when allylglycine was added as a substrate, butadiene production was observed from all PALs. However, a significant difference was observed in the amount of butadiene produced, with the highest butadiene production confirmed when using AvPAL.

Example 3

As demonstrated in Example 2, high catalytic activity for the production of butadiene was observed in the wild type AvPAL. Therefore, in order to further enhance this high catalytic activity, mutations were introduced that replaced the enzyme active sites with different amino acids. The catalytic activity of the resulting mutants was then evaluated.

Specifically, primers encoding amino acid sequences with those mutations introduced were designed and synthesized. Then, using the vector encoding the wild-type AvPAL prepared in Example 2 as a template, plasmid vectors (PAL variant vectors) were prepared capable of expressing PALs with introduced mutations in *E. coli*, using the aforementioned primers in accordance with the Gibson Assembly protocol. Then, in the above <Preparation of Enzyme Activity Measurement Medium and Measurement of Enzyme Activity>, instead of the wild-type PAL vector, the PAL variant vectors were introduced, transformants were prepared, and the enzyme activity was measured. With the butadiene production quantity when using the wild-type PAL set as 1.0, the butadiene production quantity when using the PAL variant is shown in FIG. 3.

As shown in FIG. 3, the introduction of a variety of amino acid substitutions resulted in an observed increase in butadiene production quantity compared to the wild type before the introduction, in the following amino acid substitutions:

(1) the leucine at position 108 was substituted with methionine, phenylalanine, or valine, (2) the phenylalanine at position 107 was substituted with tryptophan, (3) the leucine at position 219 was substituted with isoleucine, (4) the asparagine at position 223 was substituted with isoleucine, (5) the leucine at position 104 was substituted with alanine.

INDUSTRIAL APPLICABILITY

As described above, the present invention makes it possible to provide a method for producing an unsaturated compound having at least two carbon-carbon double bonds using an enzyme. For example, the present invention also makes it possible to produce butadiene using relatively inexpensive L-lysine as a starting material. Additionally, according to the present invention, unsaturated compounds can be produced by biosynthesis rather than by chemical synthesis, thus reducing environmental impact. Therefore, the present invention is extremely useful in the production of raw materials, including butadiene, for various synthetic polymers such as synthetic rubber.

The invention claimed is:

1. A method for producing a chain-shaped unsaturated carboxylic acid compound or a geometric isomer thereof, having the following formula (3), comprising the steps of: removing a first amino group from a chain-shaped unsaturated carboxylic acid compound or a geometric isomer thereof, having a first amino group and a first carbon-carbon double bond at a terminus, having the following formula (2), in a presence of phenylalanine ammonia lyase, and forming a second carbon-carbon double bond, wherein the phenylalanine ammonia lyase is composed of an amino acid sequence which has at least 90% identity with the amino acid sequence set forth in SEQ ID NO: 2, and

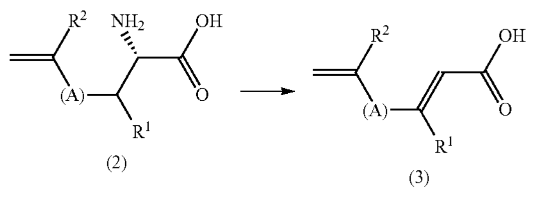

(2) (3)

in the formulas, (A) has a linear hydrocarbon group having 0 carbon atoms, which may be optionally substituted, and $R^1$ and $R^2$ each independently have a hydrogen atom, a linear or branched alkyl group having 1 to 5 carbon atoms, a linear or branched alkoxy group having 1 to 5 carbon atoms, or a hydroxy group.

2. The method according to claim 1, further comprising the steps of: removing a second amino group and a methylene group from a chain-shaped carboxylic acid compound or a geometric isomer thereof, having a first amino group and a second amino group at a terminus, having the following formula (1), in a presence of a terminal alkene generating enzyme BesC, and producing a chain-shaped unsaturated carboxylic acid compound or a geometric isomer thereof, having formula (2), wherein the compound or a geometric isomer thereof having formula (2) is used to produce the chain-shaped unsaturated carboxylic acid compound or a geometric isomer thereof, having formula (3),

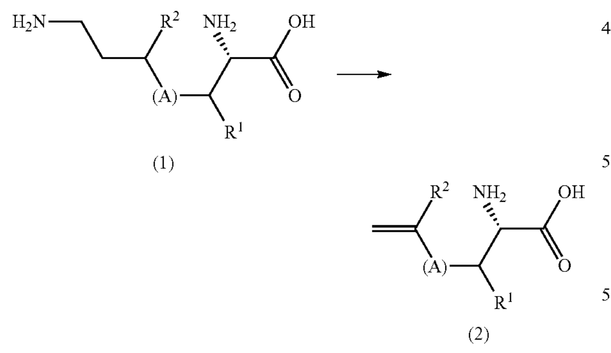

(1) (2)

wherein in the formulas, (A) has a linear hydrocarbon group having 0 carbon atoms, which may be optionally substituted, and $R^1$ and $R^2$ each independently have a hydrogen atom, a linear or branched alkyl group having 1 to 5 carbon atoms, a linear or branched alkoxy group having 1 to 5 carbon atoms, or a hydroxy group.

3. A method for producing a chain-shaped unsaturated hydrocarbon compound or a geometric isomer thereof, having the following formula (4), comprising the steps of:

removing a first amino group from a chain-shaped unsaturated carboxylic acid compound or a geometric isomer thereof, having a first amino group and a first carbon-carbon double bond at a terminus, having the following formula (2), in a presence of phenylalanine ammonia lyase, forming a second carbon-carbon double bond and producing the chain-shaped unsaturated carboxylic acid compound or a geometric isomer thereof, having formula (3), and decarboxylating a carboxyl group from the unsaturated carboxylic acid compound or a geometric isomer thereof in formula (3) formulated with ferulic acid decarboxylase

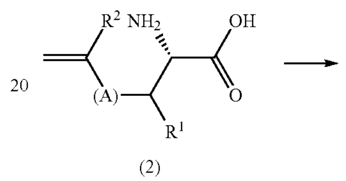

(2)

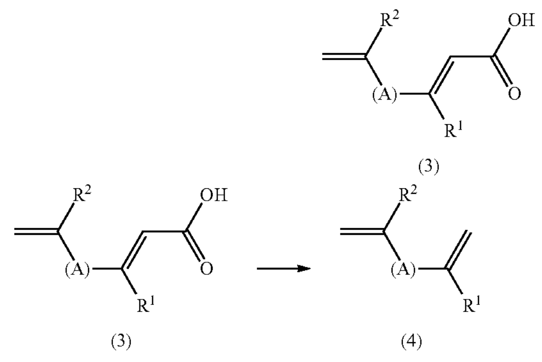

(3) (3) (4)

wherein in the formulas, (A) has a linear hydrocarbon group having 0 carbon atoms, which may be optionally substituted, and $R^1$ and $R^2$ each independently have a hydrogen atom, a linear or branched alkyl group having 1 to 5 carbon atoms, a linear or branched alkoxy group having 1 to 5 carbon atoms, or a hydroxy group.

4. The method according to claim 1, where the phenylalanine ammonia lyase is composed of an amino acid sequence which has at least 90% identity with the amino acid sequence set forth in SEQ ID NO: 2, and the amino acid sequence which has at least one of the following features (1) to (5):

(1) position 108 in the amino acid sequence set forth in SEQ ID NO: 2, or an amino acid corresponding to the position, is methionine, phenylalanine, or valine, (2) position 107 in the amino acid sequence set forth in SEQ ID NO: 2, or an amino acid corresponding to the position, is tryptophan, (3) position 219 in the amino acid sequence set forth in SEQ ID NO: 2, or an amino acid corresponding to the position, is isoleucine, (4) position 223 in the amino acid sequence set forth in SEQ ID NO: 2, or an amino acid corresponding to the position, is isoleucine, and (5) position 104 in the amino acid sequence set forth in SEQ ID NO: 2, or an amino acid corresponding to the position, is alanine.

* * * * *

SEQUENCE LISTING

```
<160> NUMBER OF SEQ ID NOS: 16

<210> SEQ ID NO 1
<211> LENGTH: 1704
<212> TYPE: DNA
```

-continued

```
<213> ORGANISM: Anabaena variabilis
<220> FEATURE:
<221> NAME/KEY: CDS
<222> LOCATION: (1)..(1704)

<400> SEQUENCE: 1

atg aag aca cta tct caa gca caa agc aaa acc tca tct caa caa ttt      48
Met Lys Thr Leu Ser Gln Ala Gln Ser Lys Thr Ser Ser Gln Gln Phe
1               5                   10                  15

tct ttt act gga aat tct tct gcc aat gta att att ggt aat cag aaa      96
Ser Phe Thr Gly Asn Ser Ser Ala Asn Val Ile Ile Gly Asn Gln Lys
            20                  25                  30

ctc aca atc aat gat gtt gca agg gta gcg cgt aat ggc acc tta gtg     144
Leu Thr Ile Asn Asp Val Ala Arg Val Ala Arg Asn Gly Thr Leu Val
        35                  40                  45

tct tta acc aat aac act gat att ttg cag ggt att cag gca tct tgt     192
Ser Leu Thr Asn Asn Thr Asp Ile Leu Gln Gly Ile Gln Ala Ser Cys
    50                  55                  60

gat tac att aat aat gct gtt gaa tct ggg gaa cca att tat gga gtg     240
Asp Tyr Ile Asn Asn Ala Val Glu Ser Gly Glu Pro Ile Tyr Gly Val
65                  70                  75                  80

aca tct ggt ttt ggc ggt atg gcc aat gtt gcc ata tcc cgt gaa caa     288
Thr Ser Gly Phe Gly Gly Met Ala Asn Val Ala Ile Ser Arg Glu Gln
                85                  90                  95

gca tct gaa ctc caa acc aac tta gtt tgg ttc ctg aaa aca ggt gca     336
Ala Ser Glu Leu Gln Thr Asn Leu Val Trp Phe Leu Lys Thr Gly Ala
            100                 105                 110

ggg aac aaa tta ccc ttg gcg gat gtg cgc gca gct atg ctc ttg cgt     384
Gly Asn Lys Leu Pro Leu Ala Asp Val Arg Ala Ala Met Leu Leu Arg
        115                 120                 125

gca aac tct cat atg cgc ggt gca tct ggc atc aga tta gaa ctt atc     432
Ala Asn Ser His Met Arg Gly Ala Ser Gly Ile Arg Leu Glu Leu Ile
    130                 135                 140

aag cgt atg gag att ttc ctt aac gct ggt gtc aca cca tat gtg tat     480
Lys Arg Met Glu Ile Phe Leu Asn Ala Gly Val Thr Pro Tyr Val Tyr
145                 150                 155                 160

gag ttt ggt tca att ggt gca agt ggt gat tta gtg cca cta tcc tac     528
Glu Phe Gly Ser Ile Gly Ala Ser Gly Asp Leu Val Pro Leu Ser Tyr
                165                 170                 175

att act ggt tca ctg ata ggc tta gat ccc agt ttt aag gtt gac ttc     576
Ile Thr Gly Ser Leu Ile Gly Leu Asp Pro Ser Phe Lys Val Asp Phe
            180                 185                 190

aac ggt aaa gaa atg gat gcg cca aca gct cta cgt caa ctg aat ttg     624
Asn Gly Lys Glu Met Asp Ala Pro Thr Ala Leu Arg Gln Leu Asn Leu
        195                 200                 205

tca ccc ttg aca ttg ttg ccg aag gaa ggc ttg gcg atg atg aac ggc     672
Ser Pro Leu Thr Leu Leu Pro Lys Glu Gly Leu Ala Met Met Asn Gly
    210                 215                 220

act tca gtc atg aca ggt att gca gca aac tgc gtc tac gat act caa     720
Thr Ser Val Met Thr Gly Ile Ala Ala Asn Cys Val Tyr Asp Thr Gln
225                 230                 235                 240

att tta act gcg atc gct atg ggc gtt cac gct cta gat atc caa gct     768
Ile Leu Thr Ala Ile Ala Met Gly Val His Ala Leu Asp Ile Gln Ala
                245                 250                 255

tta aac gga acc aat caa tca ttc cat cca ttt atc cat aat tcc aaa     816
Leu Asn Gly Thr Asn Gln Ser Phe His Pro Phe Ile His Asn Ser Lys
            260                 265                 270

cca cat cct ggt caa tta tgg gca gca gat cag atg att tct ttg tta     864
Pro His Pro Gly Gln Leu Trp Ala Ala Asp Gln Met Ile Ser Leu Leu
        275                 280                 285
```

-continued

```
gcc aat tcc cag tta gtt cgt gat gag tta gat ggt aaa cac gat tat      912
Ala Asn Ser Gln Leu Val Arg Asp Glu Leu Asp Gly Lys His Asp Tyr
    290                 295                 300

cgt gat cac gag ttg att caa gat cgt tac tca ctc cga tgc ctt ccc      960
Arg Asp His Glu Leu Ile Gln Asp Arg Tyr Ser Leu Arg Cys Leu Pro
305                 310                 315                 320

cag tat ttg ggg cca atc gtt gat gga att tcc cag att gcc aaa caa     1008
Gln Tyr Leu Gly Pro Ile Val Asp Gly Ile Ser Gln Ile Ala Lys Gln
                325                 330                 335

att gaa atc gaa atc aac tca gtc acc gat aac cca cta att gat gtt     1056
Ile Glu Ile Glu Ile Asn Ser Val Thr Asp Asn Pro Leu Ile Asp Val
            340                 345                 350

gat aac caa gct agc tat cat gga gga aat ttc ctc gga cag tac gtg     1104
Asp Asn Gln Ala Ser Tyr His Gly Gly Asn Phe Leu Gly Gln Tyr Val
        355                 360                 365

ggt atg gga atg gat cac ctg cgt tac tat att ggg tta ttg gct aaa     1152
Gly Met Gly Met Asp His Leu Arg Tyr Tyr Ile Gly Leu Leu Ala Lys
    370                 375                 380

cac cta gat gtg cag att gcc ctc ctc gcc tca cca gag ttt agc aat     1200
His Leu Asp Val Gln Ile Ala Leu Leu Ala Ser Pro Glu Phe Ser Asn
385                 390                 395                 400

gga cta cca cca tct tta tta ggc aac cga gaa cgt aaa gtc aat atg     1248
Gly Leu Pro Pro Ser Leu Leu Gly Asn Arg Glu Arg Lys Val Asn Met
                405                 410                 415

gga ctc aaa ggt ctg caa ata tgc ggt aac tca att atg cca ctg ttg     1296
Gly Leu Lys Gly Leu Gln Ile Cys Gly Asn Ser Ile Met Pro Leu Leu
            420                 425                 430

acc ttc tat gga aat tcc atc gcc gat cgc ttt cct acc cat gca gaa     1344
Thr Phe Tyr Gly Asn Ser Ile Ala Asp Arg Phe Pro Thr His Ala Glu
        435                 440                 445

caa ttt aat cag aac atc aac agt caa gga tac act tca gcg act cta     1392
Gln Phe Asn Gln Asn Ile Asn Ser Gln Gly Tyr Thr Ser Ala Thr Leu
    450                 455                 460

gcc cgc cgt tct gtg gat atc ttc cag aat tat gtg gcg atc gct ctg     1440
Ala Arg Arg Ser Val Asp Ile Phe Gln Asn Tyr Val Ala Ile Ala Leu
465                 470                 475                 480

atg ttt gga gtc caa gct gtt gac ctc cgc aca tat aaa aag act ggt     1488
Met Phe Gly Val Gln Ala Val Asp Leu Arg Thr Tyr Lys Lys Thr Gly
                485                 490                 495

cat tac gat gca cgc gcc tgt cta tca cct gca act gag cgc tta tat     1536
His Tyr Asp Ala Arg Ala Cys Leu Ser Pro Ala Thr Glu Arg Leu Tyr
            500                 505                 510

tca gca gtc cgc cac gta gtt gga caa aaa cca act tca gat cgc cca     1584
Ser Ala Val Arg His Val Val Gly Gln Lys Pro Thr Ser Asp Arg Pro
        515                 520                 525

tat att tgg aat gat aat gag caa gga ctg gat gag cat att gcc cgg     1632
Tyr Ile Trp Asn Asp Asn Glu Gln Gly Leu Asp Glu His Ile Ala Arg
    530                 535                 540

att tct gct gat atc gct gct ggt ggt gtg att gtg caa gca gtt caa     1680
Ile Ser Ala Asp Ile Ala Ala Gly Gly Val Ile Val Gln Ala Val Gln
545                 550                 555                 560

gat atc tta ccc tgc ttg cat taa                                     1704
Asp Ile Leu Pro Cys Leu His
                565
```

<210> SEQ ID NO 2
<211> LENGTH: 567
<212> TYPE: PRT
<213> ORGANISM: Anabaena variabilis

<400> SEQUENCE: 2

-continued

```
Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Asn Ser Gln Leu Val Arg Asp Glu Leu Asp Gly Lys His Asp Tyr
    290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415
```

-continued

```
Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Cys Leu His
                565


<210> SEQ ID NO 3
<211> LENGTH: 1704
<212> TYPE: DNA
<213> ORGANISM: Artificial Sequence
<220> FEATURE:
<223> OTHER INFORMATION: Codon-optimized AvPAL sequence

<400> SEQUENCE: 3

atgaaaaccc tgagccaggc acagagcaaa accagcagcc agcagtttag ctttaccggc      60

aatagcagcg caaatgtgat tattggtaat cagaaactga ccatcaatga tgttgcacgt     120

gttgcccgta atggcaccct ggttagcctg accaataata ccgatattct gcagggtatt     180

caggccagct gtgattatat caataatgca gttgaaagcg gtgaaccgat ttatggtgtt     240

accagcggtt ttggtggtat ggcaaatgtt gcaattagcc gtgaacaggc aagcgaactg     300

cagaccaatc tggtttggtt tctgaaaacc ggtgcaggta ataaactgcc gctggcagat     360

gttcgtgcag caatgctgct gcgtgcaaat agccatatgc gtggtgcaag cggtattcgt     420

ctggaactga ttaaacgcat ggaaatcttt ctgaatgccg gtgttacccc gtatgtttat     480

gaatttggta gcattggtgc cagcggtgat ctggttccgc tgagctatat taccggtagc     540

ctgattggcc tggatccgag ctttaaagtt gattttaatg gcaaagaaat ggacgcaccg     600

accgcactgc gtcagctgaa tctgagtccg ctgacactgc tgccgaaaga aggtctggca     660

atgatgaatg gcaccagcgt tatgaccggt attgcagcaa attgtgttta tgatacccag     720

attctgaccg caattgcaat gggtgttcat gcactggata ttcaggcact gaatggtaca     780

aatcagagct ttcatccgtt tatccataac agcaaaccgc atccgggtca gctgtgggca     840

gcagatcaga tgattagcct gctggccaat agccagctgg ttcgtgatga actggatggt     900

aaacatgatt atcgtgatca tgaactgatc caggatcgtt atagcctgcg ttgtctgccg     960

cagtatctgg gtccgattgt tgatggtatt agccagattg ccaagcagat tgaaattgaa    1020

attaacagcg ttaccgacaa tccgctgatt gatgttgata atcaggcaag ctatcatggt    1080

ggtaattttc tgggtcagta tgttggtatg ggtatggatc atctgcgcta ttatatcggt    1140

ctgctggcaa aacatctgga tgttcagatt gcactgctgg catcaccgga atttagcaat    1200
```

-continued ggtctgcctc cgagtctgct gggtaatcgt gaacgtaaag ttaatatggg tctgaaaggt 1260
ctgcagattt gcggtaatag cattatgccg ctgctgacct tttatggtaa tagtattgca 1320
gatcgttttc cgacacatgc cgaacagttt aaccagaata ttaacagcca gggttatacc 1380
agcgcaaccc tggcacgtcg tagcgttgat atttttcaga attatgttgc cattgcgctg 1440
atgtttggtg ttcaggcagt tgatctgcgt acctacaaaa aaaccggtca ttatgatgca 1500
cgtgcctgtc tgtcaccggc aaccgaacgt ctgtatagcg cagttcgtca tgttgttggt 1560
cagaaaccga cctcagatcg tccgtatatt tggaatgata atgaacaagg cctggatgaa 1620
catattgcac gtattagtgc agatattgca gccggtggtg ttattgttca ggccgttcag 1680
gacattctgc cgtgtctgca ttaa 1704

<210> SEQ ID NO 4
<211> LENGTH: 2202
<212> TYPE: DNA
<213> ORGANISM: Plagiochasma appendiculatum
<220> FEATURE:
<221> NAME/KEY: CDS
<222> LOCATION: (1)..(2202)

<400> SEQUENCE: 4 atg gcg gcg atg gtg atg gaa gtc ggt aca cct gca ctg gac caa gtg 48
Met Ala Ala Met Val Met Glu Val Gly Thr Pro Ala Leu Asp Gln Val
1 5 10 15 cca gca gtg aag cct ctc gtc gat ggg gct ggg gac tgg act gtc cag 96
Pro Ala Val Lys Pro Leu Val Asp Gly Ala Gly Asp Trp Thr Val Gln
20 25 30 ctg tgc ctc agt cca gtg ccg aag tcg aat gtg aac tcc gag gac cca 144
Leu Cys Leu Ser Pro Val Pro Lys Ser Asn Val Asn Ser Glu Asp Pro
35 40 45 ttg cag tgg gca aga gct gcc aaa aca att caa ggc agt cac tgg gag 192
Leu Gln Trp Ala Arg Ala Ala Lys Thr Ile Gln Gly Ser His Trp Glu
50 55 60 gaa gtg aag agc ctg gtg agc gag ttc gag cag tcg aag gag gtg gtg 240
Glu Val Lys Ser Leu Val Ser Glu Phe Glu Gln Ser Lys Glu Val Val
65 70 75 80 att caa gga gtg aca ctg aca gtt gca cag gtt acc gct gtg gct cga 288
Ile Gln Gly Val Thr Leu Thr Val Ala Gln Val Thr Ala Val Ala Arg
85 90 95 aat ccc aat gtg acc gtg gtg ctc gac gca gcc act gcc aag gag agg 336
Asn Pro Asn Val Thr Val Val Leu Asp Ala Ala Thr Ala Lys Glu Arg
100 105 110 gtg gac aag agc aac gac tgg gtc ttg cac cac atg gta aag gga act 384
Val Asp Lys Ser Asn Asp Trp Val Leu His His Met Val Lys Gly Thr
115 120 125 gac act tac ggt gtc acc act ggc ttc gga gcc act tct cac agg cgg 432
Asp Thr Tyr Gly Val Thr Thr Gly Phe Gly Ala Thr Ser His Arg Arg
130 135 140 acg aat caa gga gtg gag ctg cag cga gag ctc atc cga ttt ctt aat 480
Thr Asn Gln Gly Val Glu Leu Gln Arg Glu Leu Ile Arg Phe Leu Asn
145 150 155 160 gca ggc gtg ttg tct gac gat gcc agc atc cta ccc gtg agc acg acc 528
Ala Gly Val Leu Ser Asp Asp Ala Ser Ile Leu Pro Val Ser Thr Thr
165 170 175 aga gcc gcg atg ctg gtc aga acc aac act ctc atg cag ggg tac tcc 576
Arg Ala Ala Met Leu Val Arg Thr Asn Thr Leu Met Gln Gly Tyr Ser
180 185 190 ggc att cga tgg gaa att ttg cag acc atg cag aag ctt ctg aac aag 624

-continued

```
Gly Ile Arg Trp Glu Ile Leu Gln Thr Met Gln Lys Leu Leu Asn Lys
        195                 200                 205

cac att act ccc aga ctc cct ctg cgc gga acc atc aca gcc tcg ggg      672
His Ile Thr Pro Arg Leu Pro Leu Arg Gly Thr Ile Thr Ala Ser Gly
    210                 215                 220

gat ctt gtg ccc ttg tct tac atc gcc gga ctg ctc acc ggc cgc ccc      720
Asp Leu Val Pro Leu Ser Tyr Ile Ala Gly Leu Leu Thr Gly Arg Pro
225                 230                 235                 240

aac tct aga gct tgc acg cag gat ggc aag gtg ttg acc tcc tcg gaa      768
Asn Ser Arg Ala Cys Thr Gln Asp Gly Lys Val Leu Thr Ser Ser Glu
                245                 250                 255

gca ctg aag caa gta gga ctg ctc aag cca ttc gag ttg cag ccc aag      816
Ala Leu Lys Gln Val Gly Leu Leu Lys Pro Phe Glu Leu Gln Pro Lys
            260                 265                 270

gaa gga ctg gct atg gtg aat gga acc gcg gtt ggt gca gcg cag gcc      864
Glu Gly Leu Ala Met Val Asn Gly Thr Ala Val Gly Ala Ala Gln Ala
        275                 280                 285

tcg atg gct tgc tac gat gcc aac ttg ttg gcg gtg ttc gca gag att      912
Ser Met Ala Cys Tyr Asp Ala Asn Leu Leu Ala Val Phe Ala Glu Ile
    290                 295                 300

tcg tcc gcg ctc ttc tgt gaa gcc atg cag ggg aag cca gaa ttc aca      960
Ser Ser Ala Leu Phe Cys Glu Ala Met Gln Gly Lys Pro Glu Phe Thr
305                 310                 315                 320

gat cat ttg acg cac aag ctg aag cac cat ccg ggc cag att gaa gca     1008
Asp His Leu Thr His Lys Leu Lys His His Pro Gly Gln Ile Glu Ala
                325                 330                 335

gcc gcg gtg atg gag tgg atg ctg gac gga agc gca tac atg aaa gcg     1056
Ala Ala Val Met Glu Trp Met Leu Asp Gly Ser Ala Tyr Met Lys Ala
            340                 345                 350

gcg gcc aaa ctg cac gag act gac cct ctg aag aag ccc aag cag gac     1104
Ala Ala Lys Leu His Glu Thr Asp Pro Leu Lys Lys Pro Lys Gln Asp
        355                 360                 365

agg tac gct ctc cgc aca tcg ccg cag tgg ttg ggc cct caa att gaa     1152
Arg Tyr Ala Leu Arg Thr Ser Pro Gln Trp Leu Gly Pro Gln Ile Glu
    370                 375                 380

gtg atc cgc gcg gcc act cac tcc atc gag agg gag atc aac tcc gtg     1200
Val Ile Arg Ala Ala Thr His Ser Ile Glu Arg Glu Ile Asn Ser Val
385                 390                 395                 400

aac gac aac ccg ctc atc gat gtg tcc aga gac aag gct ctg cat gga     1248
Asn Asp Asn Pro Leu Ile Asp Val Ser Arg Asp Lys Ala Leu His Gly
                405                 410                 415

gga aat ttc caa gga acc cca att gga gtg tcg atg gac aac atg cgc     1296
Gly Asn Phe Gln Gly Thr Pro Ile Gly Val Ser Met Asp Asn Met Arg
            420                 425                 430

ttg gcg ctt gct gcc ata ggg aag ctc atg ttc gca caa atg tca gaa     1344
Leu Ala Leu Ala Ala Ile Gly Lys Leu Met Phe Ala Gln Met Ser Glu
        435                 440                 445

ttg gtg aat gat ttc tac aac agt gga ttg ccg tcg aac tta acg ggc     1392
Leu Val Asn Asp Phe Tyr Asn Ser Gly Leu Pro Ser Asn Leu Thr Gly
    450                 455                 460

ggc ccg aac ccg agc ctg gac tac ggg ttc aaa gga gcc gag atc gcc     1440
Gly Pro Asn Pro Ser Leu Asp Tyr Gly Phe Lys Gly Ala Glu Ile Ala
465                 470                 475                 480

atg gct tct tac tgc tcc gag att cag tac ctt gct aat ccg gtg act     1488
Met Ala Ser Tyr Cys Ser Glu Ile Gln Tyr Leu Ala Asn Pro Val Thr
                485                 490                 495

act cac gtg cag agt gcg gag cag cac aat cag gac gtg aat tct cta     1536
Thr His Val Gln Ser Ala Glu Gln His Asn Gln Asp Val Asn Ser Leu
            500                 505                 510
```

```
ggg ttg att tcg gct cgc aag acg gcc gaa gct att gag gtc ctg aag     1584
Gly Leu Ile Ser Ala Arg Lys Thr Ala Glu Ala Ile Glu Val Leu Lys
        515                 520                 525

ctc atg tct tca aca ttc atg gtt gcg ctc tgc cag gct gtt gat ctg     1632
Leu Met Ser Ser Thr Phe Met Val Ala Leu Cys Gln Ala Val Asp Leu
    530                 535                 540

aga cac cta gag gaa aac atg ctc gca ggc gtg aag cag gtg gtt caa     1680
Arg His Leu Glu Glu Asn Met Leu Ala Gly Val Lys Gln Val Val Gln
545                 550                 555                 560

caa gtc gcg aag aaa acc ctc ttt gcc gac gag gct gga gtg ctt ctt     1728
Gln Val Ala Lys Lys Thr Leu Phe Ala Asp Glu Ala Gly Val Leu Leu
                565                 570                 575

cct tct cgc ttc tgc gaa aag gat ctg ctc aaa gtt gtc gat gat aca     1776
Pro Ser Arg Phe Cys Glu Lys Asp Leu Leu Lys Val Val Asp Asp Thr
            580                 585                 590

ccc ccc ttc aca tac gtg gac gac gcc acc agc aaa tcg tac cct ctt     1824
Pro Pro Phe Thr Tyr Val Asp Asp Ala Thr Ser Lys Ser Tyr Pro Leu
        595                 600                 605

atg acg aaa ttg agg gag gtg ctc gtg aac cac gcc atc gag aac tcg     1872
Met Thr Lys Leu Arg Glu Val Leu Val Asn His Ala Ile Glu Asn Ser
    610                 615                 620

aag ctc gat gat aag tgt tcg gtt ttc cgc aga ata tcc gtt ttc gag     1920
Lys Leu Asp Asp Lys Cys Ser Val Phe Arg Arg Ile Ser Val Phe Glu
625                 630                 635                 640

gag gaa ttg aag act cag ttg gaa gtc acc gtc ccc cag atc aga agc     1968
Glu Glu Leu Lys Thr Gln Leu Glu Val Thr Val Pro Gln Ile Arg Ser
                645                 650                 655

caa tat gac agt ggc gtc acg tcc att gcg aat aag atc aag gaa tgc     2016
Gln Tyr Asp Ser Gly Val Thr Ser Ile Ala Asn Lys Ile Lys Glu Cys
            660                 665                 670

cgc acc ttc ccg att tac aac ttc gtt cga tct ttg gga acg aag ctt     2064
Arg Thr Phe Pro Ile Tyr Asn Phe Val Arg Ser Leu Gly Thr Lys Leu
        675                 680                 685

ctg gtc gga aca gag acg agg tct cct gga gag gac atc cag ctc gtt     2112
Leu Val Gly Thr Glu Thr Arg Ser Pro Gly Glu Asp Ile Gln Leu Val
    690                 695                 700

tac gag gcc att aac gag ggc aaa ttt gcc agt cct ttg cta tct tgc     2160
Tyr Glu Ala Ile Asn Glu Gly Lys Phe Ala Ser Pro Leu Leu Ser Cys
705                 710                 715                 720

ttg gat ggt tgg cat gga gct ccc atc cca att gat gtg tga             2202
Leu Asp Gly Trp His Gly Ala Pro Ile Pro Ile Asp Val
                725                 730
```

<210> SEQ ID NO 5
<211> LENGTH: 733
<212> TYPE: PRT
<213> ORGANISM: Plagiochasma appendiculatum

<400> SEQUENCE: 5

```
Met Ala Ala Met Val Met Glu Val Gly Thr Pro Ala Leu Asp Gln Val
1               5                   10                  15

Pro Ala Val Lys Pro Leu Val Asp Gly Ala Gly Asp Trp Thr Val Gln
            20                  25                  30

Leu Cys Leu Ser Pro Val Pro Lys Ser Asn Val Asn Ser Glu Asp Pro
        35                  40                  45

Leu Gln Trp Ala Arg Ala Ala Lys Thr Ile Gln Gly Ser His Trp Glu
    50                  55                  60

Glu Val Lys Ser Leu Val Ser Glu Phe Glu Gln Ser Lys Glu Val Val
65                  70                  75                  80
```

-continued

```
Ile Gln Gly Val Thr Leu Thr Val Ala Gln Val Thr Ala Val Ala Arg
                85                  90                  95

Asn Pro Asn Val Thr Val Val Leu Asp Ala Ala Thr Ala Lys Glu Arg
            100                 105                 110

Val Asp Lys Ser Asn Asp Trp Val Leu His His Met Val Lys Gly Thr
        115                 120                 125

Asp Thr Tyr Gly Val Thr Thr Gly Phe Gly Ala Thr Ser His Arg Arg
    130                 135                 140

Thr Asn Gln Gly Val Glu Leu Gln Arg Glu Leu Ile Arg Phe Leu Asn
145                 150                 155                 160

Ala Gly Val Leu Ser Asp Asp Ala Ser Ile Leu Pro Val Ser Thr Thr
                165                 170                 175

Arg Ala Ala Met Leu Val Arg Thr Asn Thr Leu Met Gln Gly Tyr Ser
            180                 185                 190

Gly Ile Arg Trp Glu Ile Leu Gln Thr Met Gln Lys Leu Leu Asn Lys
        195                 200                 205

His Ile Thr Pro Arg Leu Pro Leu Arg Gly Thr Ile Thr Ala Ser Gly
    210                 215                 220

Asp Leu Val Pro Leu Ser Tyr Ile Ala Gly Leu Leu Thr Gly Arg Pro
225                 230                 235                 240

Asn Ser Arg Ala Cys Thr Gln Asp Gly Lys Val Leu Thr Ser Ser Glu
                245                 250                 255

Ala Leu Lys Gln Val Gly Leu Leu Lys Pro Phe Glu Leu Gln Pro Lys
            260                 265                 270

Glu Gly Leu Ala Met Val Asn Gly Thr Ala Val Gly Ala Ala Gln Ala
        275                 280                 285

Ser Met Ala Cys Tyr Asp Ala Asn Leu Leu Ala Val Phe Ala Glu Ile
    290                 295                 300

Ser Ser Ala Leu Phe Cys Glu Ala Met Gln Gly Lys Pro Glu Phe Thr
305                 310                 315                 320

Asp His Leu Thr His Lys Leu Lys His His Pro Gly Gln Ile Glu Ala
                325                 330                 335

Ala Ala Val Met Glu Trp Met Leu Asp Gly Ser Ala Tyr Met Lys Ala
            340                 345                 350

Ala Ala Lys Leu His Glu Thr Asp Pro Leu Lys Lys Pro Lys Gln Asp
        355                 360                 365

Arg Tyr Ala Leu Arg Thr Ser Pro Gln Trp Leu Gly Pro Gln Ile Glu
    370                 375                 380

Val Ile Arg Ala Ala Thr His Ser Ile Glu Arg Glu Ile Asn Ser Val
385                 390                 395                 400

Asn Asp Asn Pro Leu Ile Asp Val Ser Arg Asp Lys Ala Leu His Gly
                405                 410                 415

Gly Asn Phe Gln Gly Thr Pro Ile Gly Val Ser Met Asp Asn Met Arg
            420                 425                 430

Leu Ala Leu Ala Ala Ile Gly Lys Leu Met Phe Ala Gln Met Ser Glu
        435                 440                 445

Leu Val Asn Asp Phe Tyr Asn Ser Gly Leu Pro Ser Asn Leu Thr Gly
    450                 455                 460

Gly Pro Asn Pro Ser Leu Asp Tyr Gly Phe Lys Gly Ala Glu Ile Ala
465                 470                 475                 480

Met Ala Ser Tyr Cys Ser Glu Ile Gln Tyr Leu Ala Asn Pro Val Thr
                485                 490                 495

Thr His Val Gln Ser Ala Glu Gln His Asn Gln Asp Val Asn Ser Leu
```

-continued

```
            500                 505                 510

Gly Leu Ile Ser Ala Arg Lys Thr Ala Glu Ala Ile Glu Val Leu Lys
        515                 520                 525

Leu Met Ser Ser Thr Phe Met Val Ala Leu Cys Gln Ala Val Asp Leu
    530                 535                 540

Arg His Leu Glu Glu Asn Met Leu Ala Gly Val Lys Gln Val Val Gln
545                 550                 555                 560

Gln Val Ala Lys Lys Thr Leu Phe Ala Asp Glu Ala Gly Val Leu Leu
                565                 570                 575

Pro Ser Arg Phe Cys Glu Lys Asp Leu Leu Lys Val Val Asp Asp Thr
            580                 585                 590

Pro Pro Phe Thr Tyr Val Asp Asp Ala Thr Ser Lys Ser Tyr Pro Leu
        595                 600                 605

Met Thr Lys Leu Arg Glu Val Leu Val Asn His Ala Ile Glu Asn Ser
    610                 615                 620

Lys Leu Asp Asp Lys Cys Ser Val Phe Arg Arg Ile Ser Val Phe Glu
625                 630                 635                 640

Glu Glu Leu Lys Thr Gln Leu Glu Val Thr Val Pro Gln Ile Arg Ser
                645                 650                 655

Gln Tyr Asp Ser Gly Val Thr Ser Ile Ala Asn Lys Ile Lys Glu Cys
            660                 665                 670

Arg Thr Phe Pro Ile Tyr Asn Phe Val Arg Ser Leu Gly Thr Lys Leu
        675                 680                 685

Leu Val Gly Thr Glu Thr Arg Ser Pro Gly Glu Asp Ile Gln Leu Val
    690                 695                 700

Tyr Glu Ala Ile Asn Glu Gly Lys Phe Ala Ser Pro Leu Leu Ser Cys
705                 710                 715                 720

Leu Asp Gly Trp His Gly Ala Pro Ile Pro Ile Asp Val
                725                 730


<210> SEQ ID NO 6
<211> LENGTH: 2203
<212> TYPE: DNA
<213> ORGANISM: Artificial Sequence
<220> FEATURE:
<223> OTHER INFORMATION: Codon-optimized PaPAL sequence

<400> SEQUENCE: 6

atggcagcaa tggtaatgga agtaggtaca ccagcattag atcaagtacc ggcagttaaa      60

ccgctggttg atggtgccgg tgattggacc gttcagctgt gtctgagtcc ggttccgaaa     120

agcaatgtta atagcgaaga tccgctgcag tgggcacgtg cagcaaaaac cattcagggt     180

agccattggg aagaagttaa aagcctggtt agcgaatttg aacagagcaa agaagttgtt     240

attcagggcg ttaccctgac cgttgcacag gttaccgcag ttgcacgtaa tccgaatgtt     300

accgttgttc tggatgcagc aaccgcaaaa gaacgtgttg ataaaagtaa tgattgggtg     360

ctgcatcata tggttaaagg caccgatacc tatggtgtta ccaccggttt tggtgcaacc     420

agccatcgtc gtaccaatca gggtgttgaa ctgcagcgtg aactgattcg ttttctgaat     480

gccggtgttc tgagtgatga tgcaagcatt ctgccggtta gcacaacccg tgcagccatg     540

ctggttcgta caaataccct gatgcagggt tatagcggta ttcgttggga aattctgcag     600

accatgcaga aactgctgaa caaacatatt acaccgcgtc tgccgctgcg tggcaccatt     660

accgcaagcg gtgatctggt tccgctgagc tatattgcag gtctgctgac cggtcgtccg     720

aatagccgtg catgtaccca ggatggtaaa gttctgacca gcagcgaagc actgaaacag     780
```

```
gttggcctgc tgaaaccgtt tgagctgcag ccgaaagaag gtctggccat ggttaatggt    840

acagcagttg gtgcagcaca ggcaagcatg gcatgttatg atgcaaatct gctggcagtt    900

tttgcagaaa tttcaagcgc actgttttgt gaagcaatgc agggtaaacc ggaatttacc    960

gatcatctga cccataaact gaaacatcat ccgggtcaga ttgaagcagc agcagttatg   1020

gaatggatgc tggatggtag cgcatatatg aaagcagccg caaaactgca tgaaaccgat   1080

ccgctgaaaa aaccgaaaca ggatcgttat gcactgcgta ccagtccgca gtggctgggt   1140

ccgcagatcg aagttattcg tgcagcgacc catagcattg aacgtgaaat taacagcgtt   1200

aatgataacc cgctgattga tgttagccgt gataaagcac tgcatggtgg taattttcag   1260

ggcaccccga ttggtgttag catggataat atgcgtctgg cactggcagc cattggtaaa   1320

ctgatgtttg cacagatgag cgaactggtg aatgatttct ataatagcgg tctgccgagt   1380

aatctgacag gcggtccgaa tccgagcctg gattatggtt ttaaaggtgc cgaaattgca   1440

atggcaagct attgtagcga aattcagtat ctggcaaatc cggttaccac acatgttcag   1500

agcgcagaac agcataatca ggatgtgaat agcctgggtc tgattagcgc acgtaaaacc   1560

gcagaagcaa ttgaagttct gaaactgatg agcagcacct ttatggttgc actgtgtcag   1620

gcagttgatc tgcgtcatct ggaagaaaac atgctggcag gcgttaaaca ggtggttcag   1680

caggttgcaa aaaaaccct gtttgcagat gaagcgggtg ttctgctgcc gagccgtttt   1740

tgtgaaaaag atctgctgaa agtggttgat gataccctc cgtttaccta tgttgatgat    1800

gcgaccagca aaagctatcc gctgatgacc aaactgcgtg aagtgctggt taatcatgca   1860

atcgaaaata gcaaactgga cgataaatgc agcgtgtttc gtcgtattag cgtgtttgaa   1920

gaagaactga aaacccagct ggaagttacc gttccgcaga ttcgtagcca gtatgatagc   1980

ggtgtgacca gcattgccaa taaaatcaaa gaatgtcgca cctttccgat ctataacttt   2040

gttcgtagcc tgggcacaaa actgctggtt ggtacggaaa cccgtagtcc gggtgaagat   2100

attcagctgg tttatgaagc aatcaacgaa ggtaaatttg caagtccgct gctgagctgt   2160

ctggatggtt ggcatggtgc accgattccg attgatgtgt aaa                      2203
```

<210> SEQ ID NO 7
<211> LENGTH: 2124
<212> TYPE: DNA
<213> ORGANISM: Arabidopsis thaliana
<220> FEATURE:
<221> NAME/KEY: CDS
<222> LOCATION: (1)..(2124)

<400> SEQUENCE: 7

```
atg gag cta tgc aat caa aac aat cac atc acc gcc gtc tcg ggc gat       48
Met Glu Leu Cys Asn Gln Asn Asn His Ile Thr Ala Val Ser Gly Asp
1               5                   10                  15

ccg ttg aac tgg aac gcg acg gcc gaa gct ttg aaa ggg agc cac ctg       96
Pro Leu Asn Trp Asn Ala Thr Ala Glu Ala Leu Lys Gly Ser His Leu
            20                  25                  30

gat gag gtg aaa cga atg gtg aaa gag tat agg aaa gag gcg gtg aag      144
Asp Glu Val Lys Arg Met Val Lys Glu Tyr Arg Lys Glu Ala Val Lys
        35                  40                  45

tta gga ggt gag act ttg acg att ggt caa gta gcc gcc gtg gct aga      192
Leu Gly Gly Glu Thr Leu Thr Ile Gly Gln Val Ala Ala Val Ala Arg
    50                  55                  60

gga gga gga gga tct acg gtg gag cta gcg gag gag gct cgt gcc gga      240
Gly Gly Gly Gly Ser Thr Val Glu Leu Ala Glu Glu Ala Arg Ala Gly
65                  70                  75                  80
```

-continued

```
gtc aag gcg agt agc gaa tgg gtg atg gag agc atg aac cga gga acg      288
Val Lys Ala Ser Ser Glu Trp Val Met Glu Ser Met Asn Arg Gly Thr
                85                  90                  95

gac agt tat gga gtt acc aca ggg ttt ggt gca act tcc cat aga aga      336
Asp Ser Tyr Gly Val Thr Thr Gly Phe Gly Ala Thr Ser His Arg Arg
            100                 105                 110

acc aaa caa ggc ggt gca ctt caa aat gag ctt att agg ttc ttg aat      384
Thr Lys Gln Gly Gly Ala Leu Gln Asn Glu Leu Ile Arg Phe Leu Asn
        115                 120                 125

gcc gga ata ttt ggc ccc ggc gcc ggg gac acg tca cac acg ttg cca      432
Ala Gly Ile Phe Gly Pro Gly Ala Gly Asp Thr Ser His Thr Leu Pro
    130                 135                 140

aag ccg aca aca aga gcg gca atg ctc gtc cgt gtc aac act ctc ctc      480
Lys Pro Thr Thr Arg Ala Ala Met Leu Val Arg Val Asn Thr Leu Leu
145                 150                 155                 160

caa ggc tac tcc ggt ata cgc ttc gag att ctc gaa gca att aca aag      528
Gln Gly Tyr Ser Gly Ile Arg Phe Glu Ile Leu Glu Ala Ile Thr Lys
                165                 170                 175

ctt ctc aac cac gaa atc act ccg tgc ctc cct ctc cgt ggc acc atc      576
Leu Leu Asn His Glu Ile Thr Pro Cys Leu Pro Leu Arg Gly Thr Ile
            180                 185                 190

acc gcc tcc ggt gac ctt gtt cct ctc tct tac atc gcc gga ctt ctc      624
Thr Ala Ser Gly Asp Leu Val Pro Leu Ser Tyr Ile Ala Gly Leu Leu
        195                 200                 205

act ggc cgt ccc aac tcc aaa gcc gtg ggt ccc tct ggt gag act ctc      672
Thr Gly Arg Pro Asn Ser Lys Ala Val Gly Pro Ser Gly Glu Thr Leu
    210                 215                 220

act gcc tct gag gcc ttt aag ctc gcc gga gta tcg tcc ttt ttc gag      720
Thr Ala Ser Glu Ala Phe Lys Leu Ala Gly Val Ser Ser Phe Phe Glu
225                 230                 235                 240

ctg cag cct aag gaa gga cta gca ctt gtg aac ggg aca gcg gtt gga      768
Leu Gln Pro Lys Glu Gly Leu Ala Leu Val Asn Gly Thr Ala Val Gly
                245                 250                 255

tcg ggt ttg gcc tca acg gtt ttg ttc gat gca aat att ttg gct gtt      816
Ser Gly Leu Ala Ser Thr Val Leu Phe Asp Ala Asn Ile Leu Ala Val
            260                 265                 270

tta tcg gaa gtt atg tct gcc atg ttc gca gag gtt atg caa ggg aaa      864
Leu Ser Glu Val Met Ser Ala Met Phe Ala Glu Val Met Gln Gly Lys
        275                 280                 285

ccg gag ttt aca gat cat ctt acg cat aag ctc aag cac cat ccc ggt      912
Pro Glu Phe Thr Asp His Leu Thr His Lys Leu Lys His His Pro Gly
    290                 295                 300

cag atc gaa gcc gcc gca att atg gaa cat ata tta gac gga agc tct      960
Gln Ile Glu Ala Ala Ala Ile Met Glu His Ile Leu Asp Gly Ser Ser
305                 310                 315                 320

tac gtt aaa gaa gct caa ctt ctc cac gaa atg gat cct ctt caa aaa     1008
Tyr Val Lys Glu Ala Gln Leu Leu His Glu Met Asp Pro Leu Gln Lys
                325                 330                 335

cct aaa caa gat cgg tac gct tta cgt acg tca cca caa tgg ctt ggg     1056
Pro Lys Gln Asp Arg Tyr Ala Leu Arg Thr Ser Pro Gln Trp Leu Gly
            340                 345                 350

ccg cag att gaa gtg atc aga gcg gct act aaa atg att gag cgt gag     1104
Pro Gln Ile Glu Val Ile Arg Ala Ala Thr Lys Met Ile Glu Arg Glu
        355                 360                 365

atc aac tct gtt aat gat aac cct ttg ata gat gtg tcg agg aac aag     1152
Ile Asn Ser Val Asn Asp Asn Pro Leu Ile Asp Val Ser Arg Asn Lys
    370                 375                 380

gcg ttg cac ggt gga aat ttc caa ggg aca ccg atc ggt gtt gcc atg     1200
Ala Leu His Gly Gly Asn Phe Gln Gly Thr Pro Ile Gly Val Ala Met
```

-continued

```
385                 390                 395                 400

gat aat tcc cgt cta gcc att gct tcc att ggg aaa ctc atg ttt gcg     1248
Asp Asn Ser Arg Leu Ala Ile Ala Ser Ile Gly Lys Leu Met Phe Ala
                405                 410                 415

cag ttt tct gaa cta gtg aac gat ttc tac aac aat ggt ttg cct tct     1296
Gln Phe Ser Glu Leu Val Asn Asp Phe Tyr Asn Asn Gly Leu Pro Ser
            420                 425                 430

aat cta tct ggt ggg aga aac cct agt ctt gat tac ggg ttt aaa ggc     1344
Asn Leu Ser Gly Gly Arg Asn Pro Ser Leu Asp Tyr Gly Phe Lys Gly
        435                 440                 445

gcg gaa ata gcc atg gct tct tat tgc tcc gag ctt cag ttc ctg gct     1392
Ala Glu Ile Ala Met Ala Ser Tyr Cys Ser Glu Leu Gln Phe Leu Ala
    450                 455                 460

aat ccc gtg acc aac cat gtc caa agc gca gag cag cat aac caa gac     1440
Asn Pro Val Thr Asn His Val Gln Ser Ala Glu Gln His Asn Gln Asp
465                 470                 475                 480

gtt aat tcc cta ggg cta atc tct agc agg aaa act gca gaa gca gtg     1488
Val Asn Ser Leu Gly Leu Ile Ser Ser Arg Lys Thr Ala Glu Ala Val
                485                 490                 495

gat atc ctc aag cta atg tcc aca acc tac tta gtc gcg ctt tgc caa     1536
Asp Ile Leu Lys Leu Met Ser Thr Thr Tyr Leu Val Ala Leu Cys Gln
            500                 505                 510

gcc gtt gat cta aga cat ctt gaa gag aat ctg aag aag gcg gtt aaa     1584
Ala Val Asp Leu Arg His Leu Glu Glu Asn Leu Lys Lys Ala Val Lys
        515                 520                 525

tca gca gtg agt cag gtg gcg aaa cgg gtc tta acc gtt ggt gcc aac     1632
Ser Ala Val Ser Gln Val Ala Lys Arg Val Leu Thr Val Gly Ala Asn
    530                 535                 540

ggg gag cta cat ccg tca agg ttc aca gaa cgt gat gtc ctc caa gtg     1680
Gly Glu Leu His Pro Ser Arg Phe Thr Glu Arg Asp Val Leu Gln Val
545                 550                 555                 560

gtt gac cga gag tac gtg ttc tca tac gca gac gat ccc tgc agc ctc     1728
Val Asp Arg Glu Tyr Val Phe Ser Tyr Ala Asp Asp Pro Cys Ser Leu
                565                 570                 575

act tac ccg cta atg cag aaa ctt aga cac att ctt gta gac cac gct     1776
Thr Tyr Pro Leu Met Gln Lys Leu Arg His Ile Leu Val Asp His Ala
            580                 585                 590

tta gcg gat cca gaa cgc gag gcc aat tcc gcg aca tcg gtt ttc cac     1824
Leu Ala Asp Pro Glu Arg Glu Ala Asn Ser Ala Thr Ser Val Phe His
        595                 600                 605

aaa atc gga gct ttt gaa gcc gag ctg aaa ctg ctt ctc cct aaa gaa     1872
Lys Ile Gly Ala Phe Glu Ala Glu Leu Lys Leu Leu Leu Pro Lys Glu
    610                 615                 620

gta gaa cgc gtc cgg gtt gaa tac gag gaa gga aca tcg gct ata gct     1920
Val Glu Arg Val Arg Val Glu Tyr Glu Glu Gly Thr Ser Ala Ile Ala
625                 630                 635                 640

aac cgg att aag gaa tgt cgg tct tat cca ttg tat cgg ttt gtc cgc     1968
Asn Arg Ile Lys Glu Cys Arg Ser Tyr Pro Leu Tyr Arg Phe Val Arg
                645                 650                 655

gat gag cta aat act gaa ctg ctt act gga gag aat gtt cgg tcg cca     2016
Asp Glu Leu Asn Thr Glu Leu Leu Thr Gly Glu Asn Val Arg Ser Pro
            660                 665                 670

gga gag gag ttt gat aaa gtg ttc tta gcg att tct gat gga aaa ctt     2064
Gly Glu Glu Phe Asp Lys Val Phe Leu Ala Ile Ser Asp Gly Lys Leu
        675                 680                 685

att gat ccg ttg ttg gaa tgt ctc aag gag tgg aac gga gct ccg gtt     2112
Ile Asp Pro Leu Leu Glu Cys Leu Lys Glu Trp Asn Gly Ala Pro Val
    690                 695                 700

tca atc tgt tga                                                     2124
```

Ser Ile Cys
705

<210> SEQ ID NO 8
<211> LENGTH: 707
<212> TYPE: PRT
<213> ORGANISM: Arabidopsis thaliana

<400> SEQUENCE: 8

```
Met Glu Leu Cys Asn Gln Asn Asn His Ile Thr Ala Val Ser Gly Asp
1               5                   10                  15

Pro Leu Asn Trp Asn Ala Thr Ala Glu Ala Leu Lys Gly Ser His Leu
            20                  25                  30

Asp Glu Val Lys Arg Met Val Lys Glu Tyr Arg Lys Glu Ala Val Lys
        35                  40                  45

Leu Gly Gly Glu Thr Leu Thr Ile Gly Gln Val Ala Ala Val Ala Arg
    50                  55                  60

Gly Gly Gly Gly Ser Thr Val Glu Leu Ala Glu Glu Ala Arg Ala Gly
65                  70                  75                  80

Val Lys Ala Ser Ser Glu Trp Val Met Glu Ser Met Asn Arg Gly Thr
                85                  90                  95

Asp Ser Tyr Gly Val Thr Thr Gly Phe Gly Ala Thr Ser His Arg Arg
            100                 105                 110

Thr Lys Gln Gly Gly Ala Leu Gln Asn Glu Leu Ile Arg Phe Leu Asn
        115                 120                 125

Ala Gly Ile Phe Gly Pro Gly Ala Gly Asp Thr Ser His Thr Leu Pro
    130                 135                 140

Lys Pro Thr Thr Arg Ala Ala Met Leu Val Arg Val Asn Thr Leu Leu
145                 150                 155                 160

Gln Gly Tyr Ser Gly Ile Arg Phe Glu Ile Leu Glu Ala Ile Thr Lys
                165                 170                 175

Leu Leu Asn His Glu Ile Thr Pro Cys Leu Pro Leu Arg Gly Thr Ile
            180                 185                 190

Thr Ala Ser Gly Asp Leu Val Pro Leu Ser Tyr Ile Ala Gly Leu Leu
        195                 200                 205

Thr Gly Arg Pro Asn Ser Lys Ala Val Gly Pro Ser Gly Glu Thr Leu
    210                 215                 220

Thr Ala Ser Glu Ala Phe Lys Leu Ala Gly Val Ser Ser Phe Phe Glu
225                 230                 235                 240

Leu Gln Pro Lys Glu Gly Leu Ala Leu Val Asn Gly Thr Ala Val Gly
                245                 250                 255

Ser Gly Leu Ala Ser Thr Val Leu Phe Asp Ala Asn Ile Leu Ala Val
            260                 265                 270

Leu Ser Glu Val Met Ser Ala Met Phe Ala Glu Val Met Gln Gly Lys
        275                 280                 285

Pro Glu Phe Thr Asp His Leu Thr His Lys Leu Lys His His Pro Gly
    290                 295                 300

Gln Ile Glu Ala Ala Ala Ile Met Glu His Ile Leu Asp Gly Ser Ser
305                 310                 315                 320

Tyr Val Lys Glu Ala Gln Leu Leu His Glu Met Asp Pro Leu Gln Lys
                325                 330                 335

Pro Lys Gln Asp Arg Tyr Ala Leu Arg Thr Ser Pro Gln Trp Leu Gly
            340                 345                 350

Pro Gln Ile Glu Val Ile Arg Ala Ala Thr Lys Met Ile Glu Arg Glu
        355                 360                 365
```

-continued

```
Ile Asn Ser Val Asn Asp Asn Pro Leu Ile Asp Val Ser Arg Asn Lys
    370                 375                 380

Ala Leu His Gly Gly Asn Phe Gln Gly Thr Pro Ile Gly Val Ala Met
385                 390                 395                 400

Asp Asn Ser Arg Leu Ala Ile Ala Ser Ile Gly Lys Leu Met Phe Ala
                405                 410                 415

Gln Phe Ser Glu Leu Val Asn Asp Phe Tyr Asn Asn Gly Leu Pro Ser
            420                 425                 430

Asn Leu Ser Gly Gly Arg Asn Pro Ser Leu Asp Tyr Gly Phe Lys Gly
        435                 440                 445

Ala Glu Ile Ala Met Ala Ser Tyr Cys Ser Glu Leu Gln Phe Leu Ala
    450                 455                 460

Asn Pro Val Thr Asn His Val Gln Ser Ala Glu Gln His Asn Gln Asp
465                 470                 475                 480

Val Asn Ser Leu Gly Leu Ile Ser Ser Arg Lys Thr Ala Glu Ala Val
                485                 490                 495

Asp Ile Leu Lys Leu Met Ser Thr Thr Tyr Leu Val Ala Leu Cys Gln
            500                 505                 510

Ala Val Asp Leu Arg His Leu Glu Glu Asn Leu Lys Lys Ala Val Lys
        515                 520                 525

Ser Ala Val Ser Gln Val Ala Lys Arg Val Leu Thr Val Gly Ala Asn
    530                 535                 540

Gly Glu Leu His Pro Ser Arg Phe Thr Glu Arg Asp Val Leu Gln Val
545                 550                 555                 560

Val Asp Arg Glu Tyr Val Phe Ser Tyr Ala Asp Asp Pro Cys Ser Leu
                565                 570                 575

Thr Tyr Pro Leu Met Gln Lys Leu Arg His Ile Leu Val Asp His Ala
            580                 585                 590

Leu Ala Asp Pro Glu Arg Glu Ala Asn Ser Ala Thr Ser Val Phe His
        595                 600                 605

Lys Ile Gly Ala Phe Glu Ala Glu Leu Lys Leu Leu Leu Pro Lys Glu
    610                 615                 620

Val Glu Arg Val Arg Val Glu Tyr Glu Glu Gly Thr Ser Ala Ile Ala
625                 630                 635                 640

Asn Arg Ile Lys Glu Cys Arg Ser Tyr Pro Leu Tyr Arg Phe Val Arg
                645                 650                 655

Asp Glu Leu Asn Thr Glu Leu Leu Thr Gly Glu Asn Val Arg Ser Pro
            660                 665                 670

Gly Glu Glu Phe Asp Lys Val Phe Leu Ala Ile Ser Asp Gly Lys Leu
        675                 680                 685

Ile Asp Pro Leu Leu Glu Cys Leu Lys Glu Trp Asn Gly Ala Pro Val
    690                 695                 700

Ser Ile Cys
705
```

<210> SEQ ID NO 9
<211> LENGTH: 2124
<212> TYPE: DNA
<213> ORGANISM: Artificial Sequence
<220> FEATURE:
<223> OTHER INFORMATION: Codon-optimized AtPAL sequence

<400> SEQUENCE: 9
atggaattat gtaatcaaaa taatcatatt acagcagtat caggtgatcc gctgaattgg      60

-continued

```
aatgcaaccg cagaagcact gaaaggtagc catctggatg aagttaaacg tatggtgaaa    120
gagtatcgta aagaggccgt taaattaggc ggtgaaaccc tgaccattgg ccaggttgca    180
gcagttgcac gcggtggtgg tggtagcacc gttgaactgg ccgaagaagc acgcgcaggc    240
gttaaagcaa gcagcgaatg ggttatggaa agcatgaatc gtggcaccga tagttatggt    300
gttaccaccg gttttggtgc aaccagccat cgtcgtacca aacaaggtgg tgcactgcag    360
aatgaactga ttcgttttct gaatgccggt atttttggtc ctggtgccgg tgataccagt    420
cataccctgc cgaaaccgac cacacgtgca gcaatgctgg ttcgtgttaa taccctgctg    480
cagggctata gcggtattcg ttttgaaatt ctggaagcca ttaccaaact gctgaaccat    540
gaaattaccc cgtgtctgcc gctgcgtggc accattaccg caagcggtga tctggttccg    600
ctgagctata ttgcaggtct gctgaccggt cgtccgaata gcaaagcagt tggtccgagt    660
ggcgaaacac tgaccgccag cgaagcattt aaactggctg gtgttagcag ctttttttgaa    720
ctgcagccga aagaaggtct ggcactggtt aatggcaccg cagttggtag cggtctggca    780
agcaccgttc tgtttgatgc aaatattctg gcagttctga gcgaagttat gagcgcaatg    840
tttgcagaag ttatgcaggg taaaccggaa tttaccgatc atctgaccca taaactgaaa    900
catcatccgg gtcagattga agcagcagca attatggaac atattctgga tggtagcagc    960
tatgttaaag aagcacagct gctgcacgaa atggatccgc tgcagaaacc gaaacaggat   1020
cgttatgcac tgcgtaccag tccgcagtgg ctgggtccgc agatcgaagt tattcgtgcc   1080
gcaaccaaaa tgattgaacg tgaaattaac agcgtgaacg ataacccgct gattgatgtt   1140
agccgtaata aagcactgca tggtggtaat tttcagggca ccccgattgg tgttgcaatg   1200
gataatagcc gtctggccat tgcaagcatt ggtaaactga tgtttgcaca gtttagcgaa   1260
ctggtgaacg atttctataa taacggtctg ccgagcaatc tgagcggtgg tcgtaatccg   1320
agcctggatt atggttttaa aggtgcagaa attgccatgg ccagctattg cagcgagctg   1380
cagtttctgg caaatccggt taccaatcat gttcagagcg cagaacagca taatcaggat   1440
gttaatagcc tgggtctgat tagcagccgt aaaacagcag aagccgttga tattctgaaa   1500
ctgatgagca ccacctatct ggttgccctg tgtcaggcag ttgatctgcg tcatctggaa   1560
gaaaatctga aaaaagcagt taaaagcgca gttagccagg tggcaaaacg tgttctgacc   1620
gttggtgcaa atggtgaact gcatccgtca cgttttaccg aacgtgatgt tctgcaggtt   1680
gttgatcgtg aatatgtttt tagctatgcc gatgatccgt gtagcctgac ctatccgctg   1740
atgcaaaaac tgcgtcatat cctggttgat catgcactgg cagatccgga acgtgaagca   1800
aatagcgcaa ccagcgtttt tcataaaatt ggtgcatttg aagccgagct gaaactgctg   1860
ctgcctaaag aagttgaacg ggttcgcgtt gaatatgaag aaggcaccag cgcaattgcc   1920
aatcgtatta aagaatgtcg ttcgtatccg ctgtatcgtt ttgttcgtga tgaactgaat   1980
acagaactgc tgacaggtga aaatgttcgt agtccgggtg aagaatttga taaagttttt   2040
ctggcgatta gcgacggcaa actgattgat cctctgctgg aatgtctgaa agaatggaat   2100
ggtgcaccgg ttagcatttg ctaa                                           2124
```

<210> SEQ ID NO 10
<211> LENGTH: 813
<212> TYPE: DNA
<213> ORGANISM: Artificial Sequence
<220> FEATURE:
<223> OTHER INFORMATION: Codon-optimized PfBesC sequence
<220> FEATURE:
<221> NAME/KEY: CDS

<222> LOCATION: (1)..(813)

<400> SEQUENCE: 10

```
atg ggt gtt cgt ccg gtt agc tat ctg gaa aat cag cgt tgt ccg cgt       48
Met Gly Val Arg Pro Val Ser Tyr Leu Glu Asn Gln Arg Cys Pro Arg
1               5                   10                  15

ggt agc cgt aaa cag gca atg agc att acc caa gaa acc ttt cag agc       96
Gly Ser Arg Lys Gln Ala Met Ser Ile Thr Gln Glu Thr Phe Gln Ser
            20                  25                  30

gaa acc gca tat gtt gtt cgt aat gaa ggt gtt gat ctg gaa ctg aaa      144
Glu Thr Ala Tyr Val Val Arg Asn Glu Gly Val Asp Leu Glu Leu Lys
        35                  40                  45

ctg ttt atg gat gag cag atc gag tat atc ctg aaa cat cgt gca acc      192
Leu Phe Met Asp Glu Gln Ile Glu Tyr Ile Leu Lys His Arg Ala Thr
    50                  55                  60

gaa cat ccg ttt ctg aat gca tat gcc gaa cat ggt ctg cct ccg gaa      240
Glu His Pro Phe Leu Asn Ala Tyr Ala Glu His Gly Leu Pro Pro Glu
65                  70                  75                  80

cag agc cag gtt ctg tac ctg gaa acc ctg cat tat ttc aaa tat ctg      288
Gln Ser Gln Val Leu Tyr Leu Glu Thr Leu His Tyr Phe Lys Tyr Leu
                85                  90                  95

ccg ttt tat gtg tgc ggc att agc acc att aca cgt gat gaa gca gtt      336
Pro Phe Tyr Val Cys Gly Ile Ser Thr Ile Thr Arg Asp Glu Ala Val
            100                 105                 110

ctg cgt acc att gca ttt aat gcc cgt gat gaa ctg ggt gaa acc cat      384
Leu Arg Thr Ile Ala Phe Asn Ala Arg Asp Glu Leu Gly Glu Thr His
        115                 120                 125

agc cat agc gat ctg tat cgt aaa ttt ctg cat gat aaa ggc atc agc      432
Ser His Ser Asp Leu Tyr Arg Lys Phe Leu His Asp Lys Gly Ile Ser
    130                 135                 140

gaa gaa caa atc gaa gcc tat aaa tgt ctg ccg agc aca cag gca ctg      480
Glu Glu Gln Ile Glu Ala Tyr Lys Cys Leu Pro Ser Thr Gln Ala Leu
145                 150                 155                 160

aat gat ggt att tgt gca ctg tat agc aaa ccg cct ctg cag aaa gca      528
Asn Asp Gly Ile Cys Ala Leu Tyr Ser Lys Pro Pro Leu Gln Lys Ala
                165                 170                 175

tta ggt ggt ctg ttt gca gat gaa gca atg agc gca agc atg gtt agc      576
Leu Gly Gly Leu Phe Ala Asp Glu Ala Met Ser Ala Ser Met Val Ser
            180                 185                 190

aaa tat aac gat ggc ctg att aaa gaa ggt gtg ggc gaa cgc ggt cgt      624
Lys Tyr Asn Asp Gly Leu Ile Lys Glu Gly Val Gly Glu Arg Gly Arg
        195                 200                 205

ttt ttt tgg acc ctg cat atg gaa gtt gaa gtg ggt cat agc aat gcc      672
Phe Phe Trp Thr Leu His Met Glu Val Glu Val Gly His Ser Asn Ala
    210                 215                 220

gtt ttt aac gtg atg gaa aaa cat ctg cag aca ccg caa gaa cgt cgc      720
Val Phe Asn Val Met Glu Lys His Leu Gln Thr Pro Gln Glu Arg Arg
225                 230                 235                 240

ctg ttt gcc gaa ggt att gaa cag tat ctg cat ctg atg gaa gtt tat      768
Leu Phe Ala Glu Gly Ile Glu Gln Tyr Leu His Leu Met Glu Val Tyr
                245                 250                 255

tgg gat ggc att gaa cgt aaa ctg aat gcc ggt ggt cgt cag taa          813
Trp Asp Gly Ile Glu Arg Lys Leu Asn Ala Gly Gly Arg Gln
            260                 265                 270
```

<210> SEQ ID NO 11
<211> LENGTH: 270
<212> TYPE: PRT
<213> ORGANISM: Artificial Sequence
<220> FEATURE:
<223> OTHER INFORMATION: Synthetic Construct

<400> SEQUENCE: 11

```
Met Gly Val Arg Pro Val Ser Tyr Leu Glu Asn Gln Arg Cys Pro Arg
1               5                   10                  15

Gly Ser Arg Lys Gln Ala Met Ser Ile Thr Gln Glu Thr Phe Gln Ser
            20                  25                  30

Glu Thr Ala Tyr Val Val Arg Asn Glu Gly Val Asp Leu Glu Leu Lys
        35                  40                  45

Leu Phe Met Asp Glu Gln Ile Glu Tyr Ile Leu Lys His Arg Ala Thr
    50                  55                  60

Glu His Pro Phe Leu Asn Ala Tyr Ala Glu His Gly Leu Pro Pro Glu
65                  70                  75                  80

Gln Ser Gln Val Leu Tyr Leu Glu Thr Leu His Tyr Phe Lys Tyr Leu
                85                  90                  95

Pro Phe Tyr Val Cys Gly Ile Ser Thr Ile Thr Arg Asp Glu Ala Val
            100                 105                 110

Leu Arg Thr Ile Ala Phe Asn Ala Arg Asp Glu Leu Gly Glu Thr His
        115                 120                 125

Ser His Ser Asp Leu Tyr Arg Lys Phe Leu His Asp Lys Gly Ile Ser
    130                 135                 140

Glu Glu Gln Ile Glu Ala Tyr Lys Cys Leu Pro Ser Thr Gln Ala Leu
145                 150                 155                 160

Asn Asp Gly Ile Cys Ala Leu Tyr Ser Lys Pro Pro Leu Gln Lys Ala
                165                 170                 175

Leu Gly Gly Leu Phe Ala Asp Glu Ala Met Ser Ala Ser Met Val Ser
            180                 185                 190

Lys Tyr Asn Asp Gly Leu Ile Lys Glu Gly Val Gly Glu Arg Gly Arg
        195                 200                 205

Phe Phe Trp Thr Leu His Met Glu Val Glu Val Gly His Ser Asn Ala
    210                 215                 220

Val Phe Asn Val Met Glu Lys His Leu Gln Thr Pro Gln Glu Arg Arg
225                 230                 235                 240

Leu Phe Ala Glu Gly Ile Glu Gln Tyr Leu His Leu Met Glu Val Tyr
                245                 250                 255

Trp Asp Gly Ile Glu Arg Lys Leu Asn Ala Gly Gly Arg Gln
            260                 265                 270
```

<210> SEQ ID NO 12
<211> LENGTH: 1512
<212> TYPE: DNA
<213> ORGANISM: Saccharomyces cerevisiae
<220> FEATURE:
<221> NAME/KEY: CDS
<222> LOCATION: (1)..(1512)
<223> OTHER INFORMATION: ScFDC

<400> SEQUENCE: 12

```
atg agg aag cta aat cca gct tta gaa ttt aga gac ttt atc cag gtc      48
Met Arg Lys Leu Asn Pro Ala Leu Glu Phe Arg Asp Phe Ile Gln Val
1               5                   10                  15

tta aaa gat gaa gat gac tta atc gaa att acc gaa gag att gat cca      96
Leu Lys Asp Glu Asp Asp Leu Ile Glu Ile Thr Glu Glu Ile Asp Pro
            20                  25                  30

aat ctc gaa gta ggt gca att atg agg aag gcc tat gaa tcc cac tta     144
Asn Leu Glu Val Gly Ala Ile Met Arg Lys Ala Tyr Glu Ser His Leu
        35                  40                  45

cca gcc ccg tta ttt aaa aat ctc aaa ggt gct tcg aag gat ctt ttc     192
```

-continued

```
Pro Ala Pro Leu Phe Lys Asn Leu Lys Gly Ala Ser Lys Asp Leu Phe
    50                  55                  60

agc att tta ggt tgc cca gcc ggt ttg aga agt aag gag aaa gga gat      240
Ser Ile Leu Gly Cys Pro Ala Gly Leu Arg Ser Lys Glu Lys Gly Asp
65                  70                  75                  80

cat ggt aga att gcc cat cat ctg ggg ctc gac cca aaa aca act atc      288
His Gly Arg Ile Ala His His Leu Gly Leu Asp Pro Lys Thr Thr Ile
                85                  90                  95

aag gaa atc ata gat tat ttg ctg gag tgt aag gag aag gaa cct ctc      336
Lys Glu Ile Ile Asp Tyr Leu Leu Glu Cys Lys Glu Lys Glu Pro Leu
            100                 105                 110

ccc cca atc act gtt cct gtg tca tct gca cct tgt aaa aca cat ata      384
Pro Pro Ile Thr Val Pro Val Ser Ser Ala Pro Cys Lys Thr His Ile
        115                 120                 125

ctt tct gaa gaa aaa ata cat cta caa agc ctg cca aca cca tat cta      432
Leu Ser Glu Glu Lys Ile His Leu Gln Ser Leu Pro Thr Pro Tyr Leu
    130                 135                 140

cat gtt tca gac ggt ggc aag tac tta caa acg tac gga atg tgg att      480
His Val Ser Asp Gly Gly Lys Tyr Leu Gln Thr Tyr Gly Met Trp Ile
145                 150                 155                 160

ctt caa act cca gat aaa aaa tgg act aat tgg tca att gct aga ggt      528
Leu Gln Thr Pro Asp Lys Lys Trp Thr Asn Trp Ser Ile Ala Arg Gly
                165                 170                 175

atg gtt gta gat gac aag cat atc act ggt ctg gta att aaa cca caa      576
Met Val Val Asp Asp Lys His Ile Thr Gly Leu Val Ile Lys Pro Gln
            180                 185                 190

cat att aga caa att gct gac tct tgg gca gca att gga aaa gca aat      624
His Ile Arg Gln Ile Ala Asp Ser Trp Ala Ala Ile Gly Lys Ala Asn
        195                 200                 205

gaa att cct ttc gcg tta tgt ttt ggc gtt ccc cca gca gct att tta      672
Glu Ile Pro Phe Ala Leu Cys Phe Gly Val Pro Pro Ala Ala Ile Leu
    210                 215                 220

gtt agt tcc atg cca att cct gaa ggt gtt tct gaa tcg gat tat gtt      720
Val Ser Ser Met Pro Ile Pro Glu Gly Val Ser Glu Ser Asp Tyr Val
225                 230                 235                 240

ggc gca atc ttg ggt gag tcg gtt cca gta gta aaa tgt gag acc aac      768
Gly Ala Ile Leu Gly Glu Ser Val Pro Val Val Lys Cys Glu Thr Asn
                245                 250                 255

gat tta atg gtt cct gca acg agt gag atg gta ttt gag ggt act ttg      816
Asp Leu Met Val Pro Ala Thr Ser Glu Met Val Phe Glu Gly Thr Leu
            260                 265                 270

tcc tta aca gat aca cat ctg gaa ggc cca ttt ggt gag atg cat gga      864
Ser Leu Thr Asp Thr His Leu Glu Gly Pro Phe Gly Glu Met His Gly
        275                 280                 285

tat gtt ttc aaa agc caa ggt cat cct tgt cca ttg tac act gtc aag      912
Tyr Val Phe Lys Ser Gln Gly His Pro Cys Pro Leu Tyr Thr Val Lys
    290                 295                 300

gct atg agt tac aga gac aat gct att cta cct gtt tcg aac ccc ggt      960
Ala Met Ser Tyr Arg Asp Asn Ala Ile Leu Pro Val Ser Asn Pro Gly
305                 310                 315                 320

ctt tgt acg gat gag aca cat acc ttg att ggt tca cta gtg gct act     1008
Leu Cys Thr Asp Glu Thr His Thr Leu Ile Gly Ser Leu Val Ala Thr
                325                 330                 335

gag gcc aag gag ctg gct att gaa tct ggc ttg cca att ctg gat gcc     1056
Glu Ala Lys Glu Leu Ala Ile Glu Ser Gly Leu Pro Ile Leu Asp Ala
            340                 345                 350

ttt atg cct tat gag gct cag gct ctt tgg ctt atc tta aag gtg gat     1104
Phe Met Pro Tyr Glu Ala Gln Ala Leu Trp Leu Ile Leu Lys Val Asp
        355                 360                 365
```

-continued

```
ttg aaa ggg ctg caa gca ttg aag aca acg cct gaa gaa ttt tgt aag     1152
Leu Lys Gly Leu Gln Ala Leu Lys Thr Thr Pro Glu Glu Phe Cys Lys
    370                 375                 380

aag gta ggt gat att tac ttt agg aca aaa gtt ggt ttt ata gtc cat     1200
Lys Val Gly Asp Ile Tyr Phe Arg Thr Lys Val Gly Phe Ile Val His
385                 390                 395                 400

gaa ata att ttg gtg gca gat gat atc gac ata ttt aac ttc aaa gaa     1248
Glu Ile Ile Leu Val Ala Asp Asp Ile Asp Ile Phe Asn Phe Lys Glu
                405                 410                 415

gtc atc tgg gcc tac gtt aca aga cat aca cct gtt gca gat cag atg     1296
Val Ile Trp Ala Tyr Val Thr Arg His Thr Pro Val Ala Asp Gln Met
            420                 425                 430

gct ttt gat gat gtc act tct ttt cct ttg gct ccc ttt gtt tcg cag     1344
Ala Phe Asp Asp Val Thr Ser Phe Pro Leu Ala Pro Phe Val Ser Gln
        435                 440                 445

tca tcc aga agt aag act atg aaa ggt gga aag tgc gtt act aat tgc     1392
Ser Ser Arg Ser Lys Thr Met Lys Gly Gly Lys Cys Val Thr Asn Cys
    450                 455                 460

ata ttt aga cag caa tat gag cgc agt ttt gac tac ata act tgt aat     1440
Ile Phe Arg Gln Gln Tyr Glu Arg Ser Phe Asp Tyr Ile Thr Cys Asn
465                 470                 475                 480

ttt gaa aag gga tat cca aaa gga tta gtt gac aaa gta aat gaa aat     1488
Phe Glu Lys Gly Tyr Pro Lys Gly Leu Val Asp Lys Val Asn Glu Asn
                485                 490                 495

tgg aaa agg tac gga tat aaa taa                                     1512
Trp Lys Arg Tyr Gly Tyr Lys
            500


<210> SEQ ID NO 13
<211> LENGTH: 503
<212> TYPE: PRT
<213> ORGANISM: Saccharomyces cerevisiae

<400> SEQUENCE: 13

Met Arg Lys Leu Asn Pro Ala Leu Glu Phe Arg Asp Phe Ile Gln Val
1               5                   10                  15

Leu Lys Asp Glu Asp Asp Leu Ile Glu Ile Thr Glu Glu Ile Asp Pro
            20                  25                  30

Asn Leu Glu Val Gly Ala Ile Met Arg Lys Ala Tyr Glu Ser His Leu
        35                  40                  45

Pro Ala Pro Leu Phe Lys Asn Leu Lys Gly Ala Ser Lys Asp Leu Phe
    50                  55                  60

Ser Ile Leu Gly Cys Pro Ala Gly Leu Arg Ser Lys Glu Lys Gly Asp
65                  70                  75                  80

His Gly Arg Ile Ala His His Leu Gly Leu Asp Pro Lys Thr Thr Ile
                85                  90                  95

Lys Glu Ile Ile Asp Tyr Leu Leu Glu Cys Lys Glu Lys Glu Pro Leu
            100                 105                 110

Pro Pro Ile Thr Val Pro Val Ser Ser Ala Pro Cys Lys Thr His Ile
        115                 120                 125

Leu Ser Glu Glu Lys Ile His Leu Gln Ser Leu Pro Thr Pro Tyr Leu
    130                 135                 140

His Val Ser Asp Gly Gly Lys Tyr Leu Gln Thr Tyr Gly Met Trp Ile
145                 150                 155                 160

Leu Gln Thr Pro Asp Lys Lys Trp Thr Asn Trp Ser Ile Ala Arg Gly
                165                 170                 175

Met Val Val Asp Asp Lys His Ile Thr Gly Leu Val Ile Lys Pro Gln
            180                 185                 190
```

```
His Ile Arg Gln Ile Ala Asp Ser Trp Ala Ala Ile Gly Lys Ala Asn
        195                 200                 205

Glu Ile Pro Phe Ala Leu Cys Phe Gly Val Pro Pro Ala Ala Ile Leu
    210                 215                 220

Val Ser Ser Met Pro Ile Pro Glu Gly Val Ser Glu Ser Asp Tyr Val
225                 230                 235                 240

Gly Ala Ile Leu Gly Glu Ser Val Pro Val Val Lys Cys Glu Thr Asn
                245                 250                 255

Asp Leu Met Val Pro Ala Thr Ser Glu Met Val Phe Glu Gly Thr Leu
            260                 265                 270

Ser Leu Thr Asp Thr His Leu Glu Gly Pro Phe Gly Glu Met His Gly
        275                 280                 285

Tyr Val Phe Lys Ser Gln Gly His Pro Cys Pro Leu Tyr Thr Val Lys
    290                 295                 300

Ala Met Ser Tyr Arg Asp Asn Ala Ile Leu Pro Val Ser Asn Pro Gly
305                 310                 315                 320

Leu Cys Thr Asp Glu Thr His Thr Leu Ile Gly Ser Leu Val Ala Thr
                325                 330                 335

Glu Ala Lys Glu Leu Ala Ile Glu Ser Gly Leu Pro Ile Leu Asp Ala
            340                 345                 350

Phe Met Pro Tyr Glu Ala Gln Ala Leu Trp Leu Ile Leu Lys Val Asp
        355                 360                 365

Leu Lys Gly Leu Gln Ala Leu Lys Thr Thr Pro Glu Glu Phe Cys Lys
    370                 375                 380

Lys Val Gly Asp Ile Tyr Phe Arg Thr Lys Val Gly Phe Ile Val His
385                 390                 395                 400

Glu Ile Ile Leu Val Ala Asp Asp Ile Asp Ile Phe Asn Phe Lys Glu
                405                 410                 415

Val Ile Trp Ala Tyr Val Thr Arg His Thr Pro Val Ala Asp Gln Met
            420                 425                 430

Ala Phe Asp Asp Val Thr Ser Phe Pro Leu Ala Pro Phe Val Ser Gln
        435                 440                 445

Ser Ser Arg Ser Lys Thr Met Lys Gly Gly Lys Cys Val Thr Asn Cys
    450                 455                 460

Ile Phe Arg Gln Gln Tyr Glu Arg Ser Phe Asp Tyr Ile Thr Cys Asn
465                 470                 475                 480

Phe Glu Lys Gly Tyr Pro Lys Gly Leu Val Asp Lys Val Asn Glu Asn
                485                 490                 495

Trp Lys Arg Tyr Gly Tyr Lys
            500
```

<210> SEQ ID NO 14
<211> LENGTH: 1512
<212> TYPE: DNA
<213> ORGANISM: Artificial Sequence
<220> FEATURE:
<223> OTHER INFORMATION: Codon-optimized ScFDC sequence

<400> SEQUENCE: 14

```
atgcgtaaac tgaatccggc actggaattt cgtgatttta ttcaggttct gaaagatgag      60

gatgacctga ttgaaatcac cgaagaaatt gatccgaatc tggaagttgg tgccattatg     120

cgtaaagcat atgaaagcca tctgcctgca ccgctgttta aaaacctgaa aggtgcaagc     180

aaagacctgt ttagcattct gggttgtccg gcaggtctgc gtagcaaaga aaaaggtgat     240
```

-continued

```
catggtcgta ttgcccatca tctgggttta gatccgaaaa ccaccatcaa agagatcatc    300

gattatctgc tggaatgcaa agagaaagaa ccgctgcctc cgattaccgt tccggttagc    360

agcgcaccgt gtaaaaccca tattctgagc gaagaaaaaa tccatctgca gagcctgccg    420

acaccgtatc tgcatgtttc agatggtggt aaatatctgc agacctatgg tatgtggatt    480

ctgcagacac cggacaaaaa atggaccaat tggagcattg cacgtggtat ggttgttgat    540

gataaacata ttaccggtct ggtgattaaa ccgcagcata ttcgtcagat tgcagatagc    600

tgggcagcaa ttggtaaagc caatgaaatt ccgtttgcac tgtgttttgg tgttccgcct    660

gcagcaattc tggtgagcag catgccgatt ccggaaggtg ttagcgaaag cgattatgtt    720

ggtgcgattc tgggtgaaag cgttccggtg gttaaatgtg aaaccaatga tctgatggtt    780

ccggcaacca gcgaaatggt ttttgaaggc accctgagcc tgaccgatac acatctggaa    840

ggtccgtttg gtgaaatgca tggttatgtg tttaaaagcc agggtcatcc gtgtccgctg    900

tataccgtta aagcaatgag ctatcgtgat aatgcaattc tgccggtgag caatccgggt    960

ctgtgtaccg atgaaaccca tacactgatt ggtagcctgg ttgccaccga agcaaaagaa   1020

ctggcaattg aaagcggtct gccgattctg gatgcattta tgccgtatga agcacaggca   1080

ctgtggctga ttctgaaagt tgatctgaaa ggactgcagg cactgaaaac cacaccggaa   1140

gaattttgta aaaaagtggg cgatatctac ttccgtacca aagttggttt tatcgtgcat   1200

gaaattattc tggtggccga tgatatcgac atcttcaact ttaaagaagt gatttgggca   1260

tacgtgaccc gtcatacacc ggttgcagat cagatggcat ttgatgatgt taccagcttt   1320

ccgctggcac cgtttgttag ccagagcagc cgtagcaaaa caatgaaagg tggcaaatgt   1380

gtgaccaact gtatttttcg tcagcagtat gaacgcagct tcgattatat cacctgtaac   1440

tttgaaaagg gctatccgaa aggtctggtg gataaagtta atgaaaactg gaaacgctac   1500

ggctataaat aa                                                       1512
```

```
<210> SEQ ID NO 15
<211> LENGTH: 570
<212> TYPE: DNA
<213> ORGANISM: Escherichia coli
<220> FEATURE:
<221> NAME/KEY: CDS
<222> LOCATION: (1)..(570)
<223> OTHER INFORMATION: Flavin prenyltransferase

<400> SEQUENCE: 15

atg aaa cga ctc att gta ggc atc agc ggt gcc agc ggc gcg att tat       48
Met Lys Arg Leu Ile Val Gly Ile Ser Gly Ala Ser Gly Ala Ile Tyr
1               5                   10                  15

ggc gtg cgc tta tta cag gtt ctg cgc gat gtc aca gat atc gaa acg       96
Gly Val Arg Leu Leu Gln Val Leu Arg Asp Val Thr Asp Ile Glu Thr
            20                  25                  30

cat ctg gtg atg agc cag gca gcg cgc cag acc tta tcc ctc gaa acg      144
His Leu Val Met Ser Gln Ala Ala Arg Gln Thr Leu Ser Leu Glu Thr
        35                  40                  45

gat ttt tct ctg cgc gaa gtg cag gca tta gcc gat gtc acg cac gat      192
Asp Phe Ser Leu Arg Glu Val Gln Ala Leu Ala Asp Val Thr His Asp
    50                  55                  60

gcg cgc gat att gcc gcc agc atc tct tcc ggt tct ttc cag acg ctg      240
Ala Arg Asp Ile Ala Ala Ser Ile Ser Ser Gly Ser Phe Gln Thr Leu
65                  70                  75                  80

ggg atg gtg att tta ccc tgt tca atc aaa acc ctt tcc ggc att gtc      288
Gly Met Val Ile Leu Pro Cys Ser Ile Lys Thr Leu Ser Gly Ile Val
                85                  90                  95
```

-continued

```
cat agc tat act gat ggc tta ctg acc cgt gcg gca gat gtg gtg ctg      336
His Ser Tyr Thr Asp Gly Leu Leu Thr Arg Ala Ala Asp Val Val Leu
            100                 105                 110

aaa gag cgt cgc ccg ttg gtg ctc tgc gtg cgt gaa aca cca ttg cac      384
Lys Glu Arg Arg Pro Leu Val Leu Cys Val Arg Glu Thr Pro Leu His
        115                 120                 125

tta ggc cat ctg cgt tta atg act cag gcg gca gaa atc ggt gcg gtg      432
Leu Gly His Leu Arg Leu Met Thr Gln Ala Ala Glu Ile Gly Ala Val
    130                 135                 140

att atg cct ccc gtt ccg gcg ttt tat cat cgc ccg caa tcc ctt gat      480
Ile Met Pro Pro Val Pro Ala Phe Tyr His Arg Pro Gln Ser Leu Asp
145                 150                 155                 160

gat gtg ata aat cag acg gtt aat cgt gtt ctt gac cag ttt gcg ata      528
Asp Val Ile Asn Gln Thr Val Asn Arg Val Leu Asp Gln Phe Ala Ile
                165                 170                 175

acc ctt cct gaa gat ctc ttt gcc cgc tgg cag ggc gca taa              570
Thr Leu Pro Glu Asp Leu Phe Ala Arg Trp Gln Gly Ala
            180                 185


<210> SEQ ID NO 16
<211> LENGTH: 189
<212> TYPE: PRT
<213> ORGANISM: Escherichia coli

<400> SEQUENCE: 16

Met Lys Arg Leu Ile Val Gly Ile Ser Gly Ala Ser Gly Ala Ile Tyr
1               5                   10                  15

Gly Val Arg Leu Leu Gln Val Leu Arg Asp Val Thr Asp Ile Glu Thr
            20                  25                  30

His Leu Val Met Ser Gln Ala Ala Arg Gln Thr Leu Ser Leu Glu Thr
        35                  40                  45

Asp Phe Ser Leu Arg Glu Val Gln Ala Leu Ala Asp Val Thr His Asp
    50                  55                  60

Ala Arg Asp Ile Ala Ala Ser Ile Ser Ser Gly Ser Phe Gln Thr Leu
65                  70                  75                  80

Gly Met Val Ile Leu Pro Cys Ser Ile Lys Thr Leu Ser Gly Ile Val
                85                  90                  95

His Ser Tyr Thr Asp Gly Leu Leu Thr Arg Ala Ala Asp Val Val Leu
            100                 105                 110

Lys Glu Arg Arg Pro Leu Val Leu Cys Val Arg Glu Thr Pro Leu His
        115                 120                 125

Leu Gly His Leu Arg Leu Met Thr Gln Ala Ala Glu Ile Gly Ala Val
    130                 135                 140

Ile Met Pro Pro Val Pro Ala Phe Tyr His Arg Pro Gln Ser Leu Asp
145                 150                 155                 160

Asp Val Ile Asn Gln Thr Val Asn Arg Val Leu Asp Gln Phe Ala Ile
                165                 170                 175

Thr Leu Pro Glu Asp Leu Phe Ala Arg Trp Gln Gly Ala
            180                 185
```